US011319282B2

(12) United States Patent
Yun et al.

(10) Patent No.: US 11,319,282 B2
(45) Date of Patent: May 3, 2022

(54) DIAMINE COMPOUND AND METHOD FOR PRODUCING SAME

(71) Applicant: LG CHEM, LTD., Seoul (KR)

(72) Inventors: Cheolmin Yun, Daejeon (KR); Jun Sik Suh, Daejeon (KR); Kyungjun Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 16/316,536

(22) PCT Filed: Aug. 11, 2017

(86) PCT No.: PCT/KR2017/008712
§ 371 (c)(1),
(2) Date: Jan. 9, 2019

(87) PCT Pub. No.: WO2018/038436
PCT Pub. Date: Mar. 1, 2018

(65) Prior Publication Data
US 2019/0292138 A1    Sep. 26, 2019

(30) Foreign Application Priority Data

Aug. 25, 2016   (KR) .................. 10-2016-0108552

(51) Int. Cl.
| | | |
|---|---|---|
| *C07C 237/40* | (2006.01) | |
| *C07C 231/02* | (2006.01) | |
| *C08G 73/10* | (2006.01) | |
| *C08G 73/14* | (2006.01) | |
| *G02B 1/04* | (2006.01) | |
| *C07C 231/12* | (2006.01) | |
| *G02B 1/10* | (2015.01) | |

(52) U.S. Cl.
CPC .......... *C07C 237/40* (2013.01); *C07C 231/02* (2013.01); *C07C 231/12* (2013.01); *C08G 73/1039* (2013.01); *C08G 73/1067* (2013.01); *C08G 73/14* (2013.01); *G02B 1/04* (2013.01); *G02B 1/10* (2013.01)

(58) Field of Classification Search
None
See application file for complete search history.

(56) References Cited

U.S. PATENT DOCUMENTS

| | | | |
|---|---|---|---|
| 3,424,728 | A | 1/1969 | Nakanishi et al. |
| 5,728,799 | A | 3/1998 | Oh |
| 6,825,355 | B2 | 11/2004 | Das et al. |
| 8,362,004 | B2 | 1/2013 | Cianci et al. |
| 9,803,054 | B2 | 10/2017 | Jung et al. |
| 9,982,103 | B2 | 5/2018 | Ju et al. |
| 2004/0077729 | A1 | 4/2004 | Ries et al. |
| 2013/0184406 | A1 | 7/2013 | Miyazaki et al. |
| 2015/0152232 | A1* | 6/2015 | Ju .............. C08J 5/18 524/442 |
| 2016/0137787 | A1 | 5/2016 | Oka et al. |
| 2016/0222249 | A1 | 8/2016 | Choi et al. |
| 2018/0009946 | A1 | 1/2018 | Jung et al. |
| 2019/0010292 | A1 | 1/2019 | Yun et al. |
| 2019/0016849 | A1 | 1/2019 | Yun et al. |
| 2019/0023846 | A1 | 1/2019 | Yun et al. |
| 2019/0048143 | A1 | 2/2019 | Hong et al. |
| 2019/0077915 | A1 | 3/2019 | Yun et al. |

FOREIGN PATENT DOCUMENTS

| | | |
|---|---|---|
| CN | 104411744 A | 3/2015 |
| CN | 105492496 A | 4/2016 |
| EP | 0837896 A1 | 4/1998 |
| JP | 1994-175138 A | 6/1994 |
| JP | 06345868 | * 12/1994 |
| JP | H06-345868 A | 12/1994 |
| JP | H07-84429 B2 | 9/1995 |
| JP | H11-508938 A | 8/1999 |
| JP | 2001-522800 A | 11/2001 |
| JP | 2005-255981 A | 9/2005 |
| JP | 2010-150379 A | 7/2010 |
| JP | 2013-537193 A | 9/2013 |
| JP | 2014-125455 A | 7/2014 |
| JP | 2014-173071 A | 9/2014 |
| JP | 2016-518495 A | 6/2016 |
| JP | 2018-538397 A | 12/2018 |
| JP | 2019-502786 A | 1/2019 |
| JP | 2019-505604 A | 2/2019 |

(Continued)

OTHER PUBLICATIONS

Machine Translation of Kaneko et al. (JP 06345868), 1994.*
STN abstractor Kaneko et al. (JP 06345868), 1994.*
Human English Translation of Kaneko et al. (JP 06345868, pub date Dec. 20, 1994). (Year: 1994).*
Ni et al. (Journal of Industrial and Engineering Chemistry, 2015, (28), p. 16) (Year: 2015).*
Chemical Abstract compounds. STN express RN161301-82-2, 2 pages.
Search Report issued for International Application No. PCT/KR2017/008712 dated Nov. 13, 2017, 3 pages.
Office Action issued for Taiwanese Patent Application No. 106125667 dated Mar. 31, 2018, 11 pages.
CAS registration No. 161301-82-2 (1995), 1 page.
Kang et al., "Preparation and properties of Aromatic Polyamide Homologs Containing Chlorine Substituents",J. Appl. Polym. Sci. 2000, v.77, pp. 1387-1392.

(Continued)

*Primary Examiner* — Sudhakar Katakam
*Assistant Examiner* — Jennifer C Sawyer
(74) *Attorney, Agent, or Firm* — Rothwell, Figg, Ernst & Manbeck, P.C.

(57) ABSTRACT

The present invention provides a novel diamine compound capable of producing a polymer which exhibits greatly enhanced mechanical properties and heat resistance while maintaining transparency. A film including a polymer produced using the diamine compound has excellent transparency, heat resistance, mechanical strength and flexibility, and thus can be used in various fields, such as in a device substrate, a display cover substrate, an optical film, an Integrated circuit (IC) package, an adhesive film, a multilayer flexible printed circuit (FPC), a tape, a touch panel and an optical disc protection film, and the like.

11 Claims, 5 Drawing Sheets

(56) References Cited

FOREIGN PATENT DOCUMENTS

| | | |
|---|---|---|
| JP | 2019-506462 A | 3/2019 |
| JP | 2019-512559 A | 5/2019 |
| KR | 10-2006-0041851 A | 5/2006 |
| KR | 10-0655766 B1 | 12/2006 |
| KR | 10-2014-0135915 A | 11/2014 |
| KR | 10-1535343 B1 | 7/2015 |
| TW | 200535120 A | 11/2005 |
| TW | 201400531 A | 1/2014 |
| TW | 201500461 A | 1/2015 |
| WO | 2012-043186 A1 | 4/2012 |
| WO | 2013-144992 A1 | 10/2013 |
| WO | 2014-208704 A1 | 12/2014 |

OTHER PUBLICATIONS

Ríos Martínez et al., "Lowering the pKa of a bisimidazoline lead with halogen atoms results in improved activity and selectivity against Trypanosoma brucei in vitro", Eur. J. Med. Chem. 2015, v.101, pp. 806-817.

Ogata et al., "Kinetics of Alkaline Hydrolysis of some Aromatic Nitriles" The Chemical Society of Japan, 1949, V. 70 (1-2), pp. 32-34, with English abstract, 4 pages.

Koenigsmann et al., "Structure-function relationships in single molecule rectification by N-phenylbenzamide derivatives", New J. Chem. 2016, v.40, pp. 7373-7378.

Search Report issued for European Patent Application No. 17 843.856.0 dated Nov. 12, 2020, 14 pages.

Office Action issued for Japanese Patent Application No. 2020-070912 dated Apr. 6, 2021, with English translation, 7 pages.

\* cited by examiner

DIAMINE COMPOUND AND METHOD FOR PRODUCING SAME

TECHNICAL FIELD

The application is a 35 U.S.C. § 371 National Phase Entry Application from PCT/KR2017/008712, filed on Aug. 11, 2017, and designating the United States, which claims the benefits of priority to Korean Patent Application No. 10-2016-0108552, filed on Aug. 25, 2016 which are incorporated herein by reference in their entirety for all purpose.

The present invention relates to a diamine compound having a novel structure, a method for manufacturing thereof, and a method for manufacturing a polymer by using the diamine compound.

BACKGROUND ART

Polyimide (PI) is a polymer having relatively low crystallinity or amorphous structure, and it has advantages such as easy manufacturing process, easy process to make a thin film and no crosslinkable moieties necessary for curing, as well as polymeric properties such as high transparency, excellent thermal and chemical resistance, excellent mechanical and electrical properties, and dimensional stability due to its rigid chain structure. The polyimide is now widely used as an electrical and electronical material for the field of car and aerospace, a flexible circuit board, a liquid crystal alignment film for LCD, an adhesive as well as a coating agent.

However, even though the polyimide is a high performance polymer with excellent thermal stability, mechanical properties, chemical resistance and electrical properties, it does not satisfy the basic requirements for the display area such as colorless transparency, and the thermal expansion coefficient should be further lowered. For example, KAPTON sold by Dupont has a low thermal coefficient of about 30 ppm/° C., but it still does not meet the requirement for the plastic substrate. Therefore, now studies for minimizing change in thermal history and optical properties while maintaining the basic properties of the polyimide are underway.

In general, aromatic polyimide has a unique color of dark brown. The reason for this is that electrons can be excited due to a σ electron, a π electron, a nonbonding unshared electron pair within the imide structure, and it can be explained by the theory of charge transfer complex (hereinafter, called CT-complex) induced by π electrons of benzene within a main chain of the polyimide.

In general, the polyimide absorbs light of the wavelength below 400 nm to 500 nm of visible light region, and therefore it shows a complementary color of yellow to red. In order to lower the CT-complex that is an disadvantage of the polyimide, a method of introducing an electron-withdrawing functional group having relatively strong electronegativity such as trifluoromethyl (—$CF_3$), sulfone (—$SO_2$) and ether (—O—) to the main chain of the polyimide is used to lower resonance effect by limiting the movement of π electron. Also introducing a cyclo-olefin structure instead of benzene to the main chain of the polyimide can reduce π electron density to manufacture a colorless transparent polyimide film.

Meanwhile, polyamide-imide has been widely used as an industrial material in the electrical, mechanical, electronic and aerospace fields due to its excellent properties such as thermal resistance, mechanical strength and electrical property. Also, in general, structure of the polyamide-imide is different from that of the polyimide and is known to be soluble in an organic solvent, allowing for the application for an enamel varnish, a coating agent for electrical insulation and paint, which need solution casting.

However, for the application in the display area, it is still necessary to develop a polymer for the flexible display with lower thermal expansion coefficient, high solubility, transparency as well as thermal stability.

DISCLOSURE

Technical Problem

One object of the present invention is to provide a novel diamine compound containing a structure which can enhance colorless transparency of a polymer as well as excellent mechanical properties, and a method for manufacturing thereof.

Another object of the present invention is to provide a method for manufacturing a polymer by using the diamine compound.

Further another object of the present invention is to provide a transparent film containing the polymer.

Technical Solution

In order to solve the above-mentioned technical problems, the present invention provides a diamine compound represented by the following Chemical Formula 1:

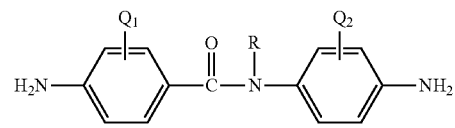

[Chemical Formula 1]

wherein, $Q_1$ and $Q_2$ are each independently selected from a fluoride atom (F), a $C_{1-10}$ fluoroalkyl group, a $C_{6-30}$ fluoroaryl group and a cyano group (CN); and R is a hydrogen atom, a $C_{1-10}$ alkyl group or a $C_{6-30}$ aryl group.

According to one embodiment, $Q_1$ and $Q_2$ may be each independently selected from a $C_{1-5}$ fluoroalkyl group.

According to one embodiment, the diamine compound of Chemical Formula 1 may contain the structure of the following Chemical Formula 1a:

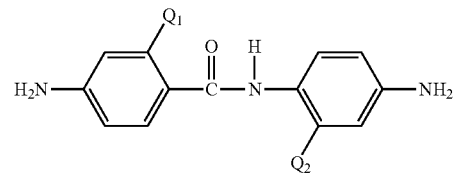

[Chemical Formula 1a]

wherein, $Q_1$ and $Q_2$ have the same meanings as defined in the Chemical Formula 1.

According to one embodiment, $^1$H-NMR of the diamine compound may be form peaks at the positions corresponding to 9.48±1.0 ppm(1H), 7.31±1 ppm(1H), 7.02±0.2 ppm(1H), 6.94±0.2 ppm(1H), 6.90±0.2 ppm(1H), 6.81±0.2 ppm(2H), 5.86±0.2 ppm(2H) and 5.57±0.2 ppm(2H).

In order to solve another problem of the present invention, the present invention provides a method for manufacturing the novel diamine compound which comprises the following steps of:

reacting the compound of the following Chemical Formula 3 and the compound of the following Chemical Formula 4 to manufacture the compound of Chemical Formula 5; and hydrogenating the compound of Chemical Formula 5 to form the compound of Chemical Formula 6:

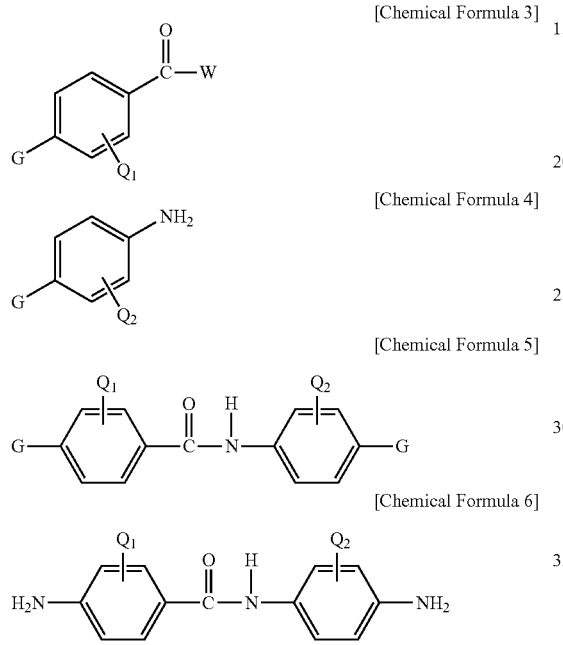

[Chemical Formula 3]

[Chemical Formula 4]

[Chemical Formula 5]

[Chemical Formula 6]

wherein, $Q_1$ and $Q_2$ are each independently selected from a fluoride atom (F), a $C_{1-10}$ fluoroalkyl group, a $C_{6-30}$ fluoroaryl group and a cyano group (CN);

W is selected from a hydroxyl group (—OH), a fluoro group (—F), a chloro group (—Cl), a bromo group (—Br), an iodo group (—I) and an alkoxyl group (—OR'), wherein R' is a $C_{1-3}$ alkyl group; and G is selected from —$NO_2$ or —NH (PG), wherein PG is a protecting group selected from the group consisting of carbobenzyloxy (Cbz), p-methoxybenzyl carbonyl (Moz), tert-butyloxycarbonyl (BOC), 9-fluorenylmethyloxycarbonyl (FMOC), acetyl (Ac), benzoyl (Bz), benzyl (Bn), Carbamate, p-methoxybenzyl (PMB), 3,4-dimethoxybenzyl (DMPM), p-methoxyphenyl (PMP), tosyl (Ts) and nosyl (Ns).

According to one embodiment, the manufacturing method may comprise the following steps of:

hydrolyzing the compound represented by Chemical Formula A of the following Reaction Formula 1 to manufacture the compound of Chemical Formula B;

reacting the compound represented by Chemical Formula B and the compound represented by Chemical Formula C of the following Reaction Formula 2 to manufacture the dinitro compound represented by Chemical Formula D; and hydrogenating the dinitro compound represented by Chemical Formula D of the following Reaction Formula 2 to manufacture the diamine compound represented by Chemical Formula 1a:

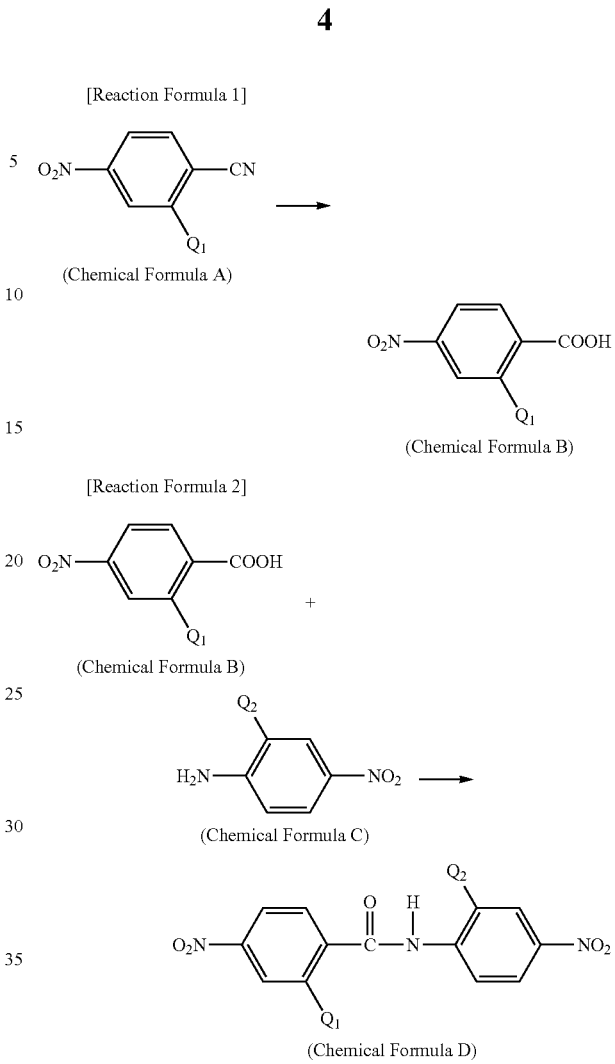

wherein, $Q_1$ and $Q_2$ is a $C_{1-5}$ fluoroalkyl group.

According to one embodiment, the manufacturing method may comprise the following steps of:

substituting carboxylic acid of the compound represented by Chemical Formula E of the following Reaction Formula 3 with chloride to manufacture the compound of Chemical Formula F;

reacting the compound represented by Chemical Formula F and the compound represented by Chemical Formula G of the following Reaction Formula 4 to manufacture the compound represented by Chemical Formula H; and hydrogenating the compound represented by Chemical Formula H of the following Reaction Formula 4 to manufacture the diamine compound represented by Chemical Formula 1a:

[Reaction Formula 3]

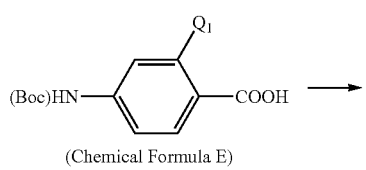

(Chemical Formula E)

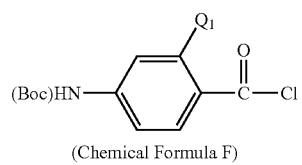

(Chemical Formula F)

[Reaction Formula 4]

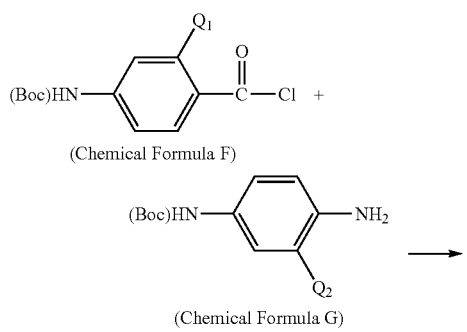

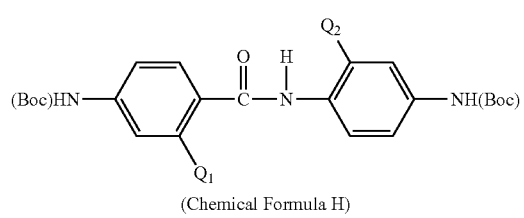

[Chemical Formula 1a]

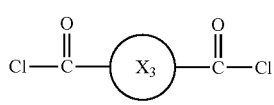

wherein, $Q_1$ and $Q_2$ are a $C_{1-5}$ fluoroalkyl group.

The novel diamine compound manufactured by the manufacturing method according to the present invention may be synthesized in the purity of 99.0% or higher.

In order to solve another problem of the present invention, the present invention provides a polymer obtained from a polymerization reaction by using the diamine compound as a monomer.

In order to solve further another problem of the present invention, the present invention provides a method for manufacturing a polymer comprising a step of reacting the diamine compound with at least one selected from the tetracarboxylic dianhydride of the following Chemical Formula 10, the dicarboxylic acid of Chemical Formula 12 or the dicarboxylic dichloride of Chemical Formula 13:

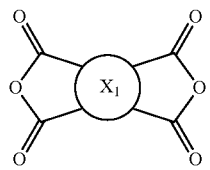

[Chemical Formula 10]

wherein,
$X_1$ is a tetravalent organic group containing a $C_{6-30}$ aromatic ring or a $C_{4-30}$ aliphatic ring,

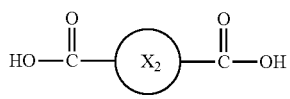

[Chemical Formula 12]

wherein,
$X_2$ is a divalent organic group containing a $C_{6-30}$ aromatic ring or a $C_{4-30}$ aliphatic ring,

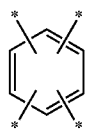

[Chemical Formula 13]

wherein,
$X_3$ is a divalent organic group containing a $C_{6-30}$ aromatic ring or a $C_{4-30}$ aliphatic ring.

According to one embodiment, the tetracarboxylic dianhydride of Chemical Formula 10 may be one selected from the compounds of the following Chemical Formulas 11a to 11i:

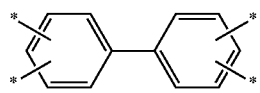 (11a)

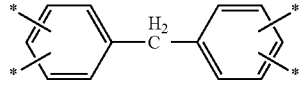 (11b)

(11c)

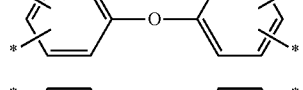 (11d)

(11e)

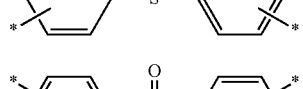 (11f)

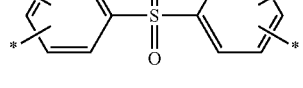

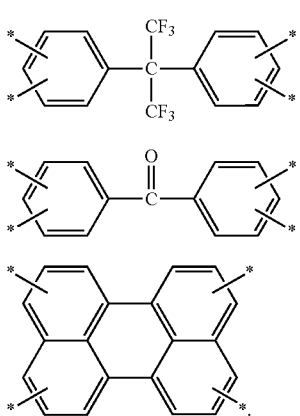

According to one embodiment, the present invention provides a method for manufacturing a polymer, wherein the compounds of Chemical Formulas 12 and 13 are the compounds represented by the following Chemical Formulas 12a and 13a.

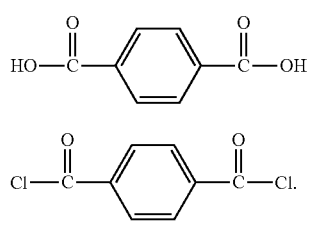

[Chemical Formula 12a]

[Chemical Formula 13a]

According to one embodiment, the polymer manufactured by the manufacturing method may be one selected from the group consisting of polyimide, polyamic acid, polyamide and polyamide-imide.

Further, the present invention provides a polymer manufactured by the manufacturing method and a transparent film comprising the polymer.

According to one embodiment, the transparent film may have the haze of 2 or less, the yellowness index of 20 or less, and the pencil hardness of 2H or more.

Further, the present invention provides a display device comprising the transparent film.

Advantageous Effects

The present invention provides a novel diamine compound which can manufacture a polymer with largely enhanced mechanical properties and heat resistance while maintaining transparency. A film comprising the polymer manufactured with the diamine compound can be used in various fields such as a substrate for a device, a cover substrate for a display, an optical film, an Integrated circuit (IC) package, an adhesive film, a multi-layer flexible printed circuit (FPC), a tape, a touch panel and a protection film for an optical disk due to its excellent transparency, heat resistance, mechanical strength and flexibility.

BEST MODE CARRYING OUT THE INVENTION

Figure 1:
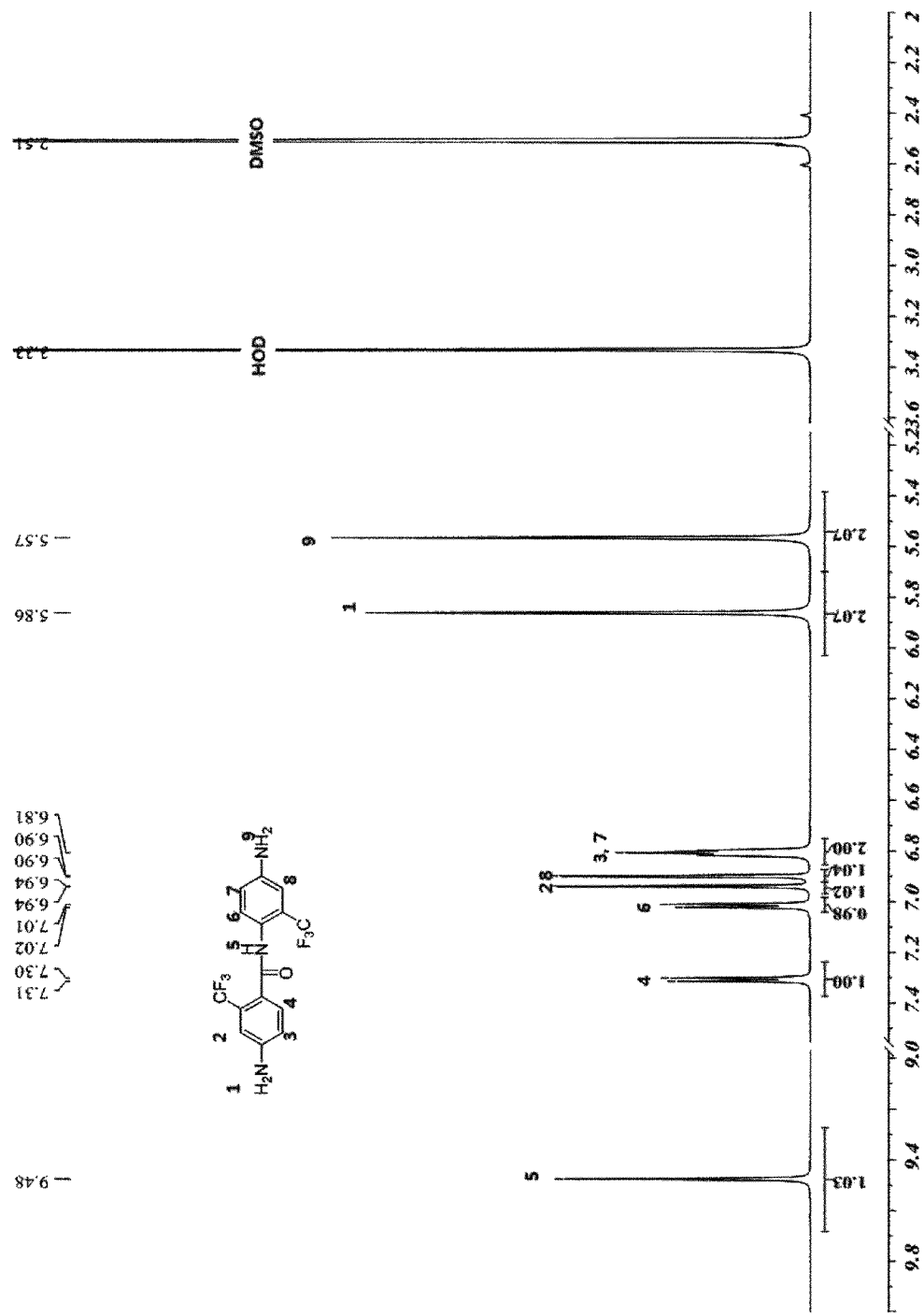
FIG. 1 is the result of $^1$H NMR analysis of the diamine compound manufactured according to Example 1 of the present invention.

Various changes in form and details may be made to the presently disclosed embodiment and thus should not be construed as being limited to the aspects set forth herein. The presently disclosed embodiment is not limited to the aspects described in the present description, and thus it should be understood that the presently disclosed embodiment does not include every kind of variation example or alternative equivalent included in the spirit and scope of the presently disclosed embodiment. Also, while describing the aspects, detailed descriptions about related well-known functions or configurations that may diminish the clarity of the points of the aspects of the presently disclosed embodiment will be omitted.

Unless particularly stated otherwise herein, all the compounds or organic groups may be substituted or unsubstituted. Herein, the term 'substituted' means that at least one hydrogen atom in such a compound or substituent has been replaced by any one substituent selected from the group consisting of a halogen atom, a $C_{1-10}$ alkyl group, a halogenated alkyl group, a $C_{3-30}$ cycloalkyl group, a $C_{6-30}$ aryl group, a hydroxyl group, a $C_{1-10}$ alkoxyl group, a carboxyl group, an aldehyde group, an epoxy group, a cyano group, a nitro group, an amino group, a sulfonic acid group and derivatives thereof.

Further, unless particularly stated otherwise herein, the term 'combination thereof' means that two or more functional groups are bonded by a single bond, a double bond, a triple bond or a linking group such as a $C_{1-10}$ alkylene group (e.g., methylene group (—$CH_2$—), ethylene group (—$CH_2CH_2$—), etc.), a $C_{1-10}$ fluoroalkylene group (e.g., fluoromethylene group (—$CF_2$—), a perfluoroethylene group (—$CF_2CF_2$—), etc.), a hetero atom such as N, O, P, S or Si, or a functional group containing thereof (e.g., intramolecular carbonyl group (—C=O—), ether group (—O—), ester group (—COO—), heteroalkylene group containing —S—, —NH—, —N=N—, etc.), or two or more functional groups are connected by condensation.

Polyimide is a polymer composed of rigid aromatic groups and imide bonds, thereby having excellent mechanical properties and heat resistance, and it is variously used in many industrial fields based on such characteristics. However, the existing polyimide may be yellowed because it absorbs light in part of visible light region by electron transfer in chains and between chains, and the yellowness may hinder possibility as a highly heat resistant and transparent material for a display. This yellowness may be caused by charge transfer complex, and it may be more severely occurred as more packing is happened between the polyimide polymer chains. In order to solve the yellowness problem, the present invention may provide a method for minimizing charge transfer by introducing a repeating unit containing other group to a polyimide main chain to hinder the packing between the polyimide chains. As the repeating unit, polyamide may be introduced to a polyimide chain. The polymer also has excellent mechanical properties and heat resistance like the polyimide and therefore, it can prevent the packing between the polymer chains during copolymerization with the polyimide and further reduce the charge transfer so as to improve optical properties. However, in terms of the polyamide structure having partial crystalline structure caused by rigid chain structure and hydrogen bonds between chain structures, transparency may be deteriorated, and also cloudiness may occur due to incompatibility between the crystalline structure of the polyamide and non-crystalline structure of the polyimide.

In order to solve the conventional problems, the present invention provides a diamine compound represented by the following Chemical Formula 1:

[Chemical Formula 1]

wherein, $Q_1$ and $Q_2$ are each independently selected from a fluoride atom (F), a $C_{1-10}$ fluoroalkyl group, a $C_{6-30}$ fluoroaryl group and a cyano group (CN), and preferably, $Q_1$ and $Q_2$ are each independently selected from a $C_{1-5}$ fluoroalkyl group, for example, a trifluoromethyl group, R is a hydrogen atom, a $C_{1-10}$ alkyl group or a $C_{6-30}$ aryl group, preferably a hydrogen atom.

The diamine structure according to the present invention can allow a polymerized polymer showing excellent mechanical properties and heat resistance by having a rigid structure consisting of a benzene ring and an amide group, and also can increase colorless transparency by introducing a specific substituent with high electronegativity to the benzene ring. For example, an atom with high electronegativity such as a fluoride substituent is introduced to minimize the charge transfer and to reduce yellowness index, or a phenyl group is introduced to prevent a hydrogen bonding between amide groups and to increase the distance between the chains at the same time, thereby also minimizing the charge transfer and reducing crystallinity. Therefore, the diamine can increase the colorless transparency of a polymer and particularly, it can be applied to polyamide-imide, polyimide and the like having high mechanical properties and heat resistance to exhibit excellent transparency.

The compound of Chemical Formula 1 may be, for example, the compound of the following Chemical Formula 1a:

[Chemical Formula 1a]

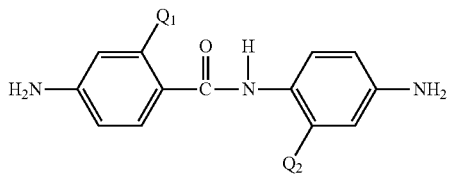

wherein, $Q_1$ and $Q_2$ have the same meanings as defined in Chemical Formula 1.

The transparency and heat resistance of the polymer can be further maximized by substituting $Q_1$ and $Q_2$ at the position shown in the structure of Chemical Formula 1a.

For example, when the $Q_1$ and $Q_2$ substituents are substituted at the position shown in the Chemical Formula 1a, the reactivity may be optimized because steric hindrance caused by the substituents is little during the polymer polymerization reaction. Further, in terms of molecular structure or electronegativity, the position are the most suitable substitution positions which can inhibit intermolecular hydrogen bonding by amide, and the position can more effectively inhibit the increase of packing density caused by the intermolecular hydrogen bonding, thereby remarkably reducing the yellowness problem which can be caused by the increase of packing density. Further, in-plane orientation can be induced by properly inhibiting the rotation of a benzene of the diamine molecule, and therefore, it may be more advantageous to form a structure with the enhance heat resistance. Thus, the position of the substituent as shown above can optimize the colorless transparency and heat resistance due to the diamine structure according to the present invention.

When $Q_1$ and $Q_2$ contains a fluoroalkyl group and has the substitution position as shown in the Chemical Formula 1a, $^1$H-NMR of the diamine compound may form peaks at the positions corresponding to 9.48±1.0 ppm(1H), 7.31±1.0 ppm(1H), 7.02±0.2 ppm(1H), 6.94±0.2 ppm(1H), 6.90±0.2 ppm(1H), 6.81±0.2 ppm(2H), 5.86±0.3 ppm(2H) and 5.57±0.3 ppm(2H).

In the present invention, the diamine compound represented by Chemical Formula 1 may be manufactured by the following reaction.

The compound may be manufactured by a method comprising the following steps of:

reacting the compound of the following Chemical Formula 3 and the compound of the following Chemical Formula 4 to manufacture the compound of Chemical Formula 5; and hydrogenating the compound of Chemical Formula 5 to form the compound of Chemical Formula 6:

[Chemical Formula 3]

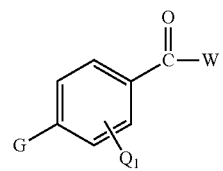

[Chemical Formula 4]

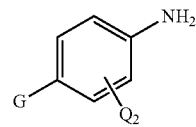

[Chemical Formula 5]

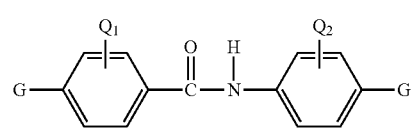

[Chemical Formula 6]

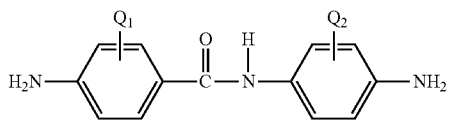

wherein, $Q_1$ and $Q_2$ are each independently selected from a fluoride atom (F), a $C_{1-10}$ fluoroalkyl group, a $C_{6-30}$ fluoroaryl group and a cyano group (CN), W is selected from a hydroxyl group (—OH), a fluoro group (—F), a chloro group (—Cl), a bromo group (—Br), an iodo group (—I) and an alkoxyl group (—OR'), wherein R' is a $C_{1-3}$ alkyl group; and G is selected from —$NO_2$ or —NH (PG), wherein PG is a protecting group selected from the group consisting of carbobenzyloxy (Cbz), p-methoxybenzyl carbonyl (Moz), tert-butyloxycarbonyl (BOC), 9-fluorenylmethyloxycarbonyl (FMOC), acetyl (Ac), benzoyl (Bz), benzyl (Bn), Carbamate, p-methoxybenzyl (PMB), 3,4-dimethoxybenzyl (DMPM), p-methoxyphenyl (PMP), tosyl (Ts) and nosyl (Ns). Preferably, it may be selected from Moz and Boc.

For example, the diamine compound may be manufactured by a method comprising the reaction of the following Reaction Formula 1 to Reaction Formula 2.

The diamine compound may be manufactured by the method comprising the following steps of:

hydrolyzing the compound represented by Chemical Formula A of the following Reaction Formula 1 to manufacture the compound of Chemical Formula B;

reacting the compound represented by Chemical Formula B and the compound represented by Chemical Formula C of the following Reaction Formula 2 to manufacture the dinitro compound represented by Chemical Formula D; and hydrogenating the dinitro compound represented by Chemical Formula D of the following Reaction Formula 2 to manufacture the diamine compound represented by Chemical Formula 1a.

[Reaction Formula 1]

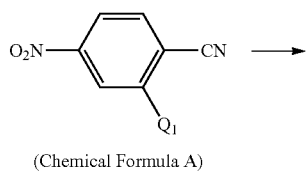 → 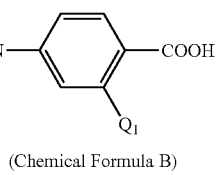

(Chemical Formula A)     (Chemical Formula B)

[Reaction Formula 2]

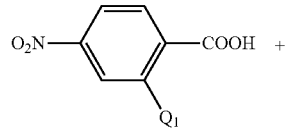 +

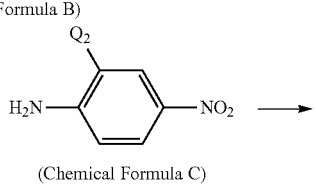 →

(Chemical Formula B)

(Chemical Formula C)

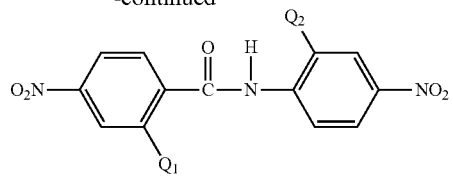

(Chemical Formula D)

Further, the diamine compound also may be manufactured by a method comprising the reaction of the following Reaction Formula 3 to Reaction Formula 4.

The diamine compound may be manufactured by the method comprising the following steps of:

substituting carboxylic acid of the compound represented by Chemical Formula E of the following Reaction Formula 3 with chloride to manufacture the compound of Chemical Formula F;

reacting the compound represented by Chemical Formula F and the compound represented by Chemical Formula G of the following Reaction Formula 4 to manufacture the compound represented by Chemical Formula H; and hydrogenating the compound represented by Chemical Formula H of the following Reaction Formula 4 to manufacture the diamine compound represented by Chemical Formula 1a.

[Reaction Formula 3]

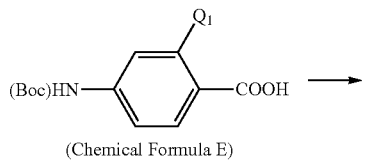 →

(Chemical Formula E)

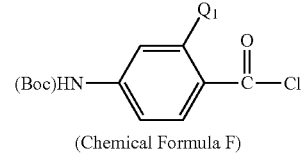

(Chemical Formula F)

[Reaction Formula 4]

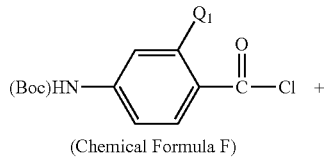 +

(Chemical Formula F)

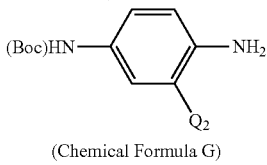 →

(Chemical Formula G)

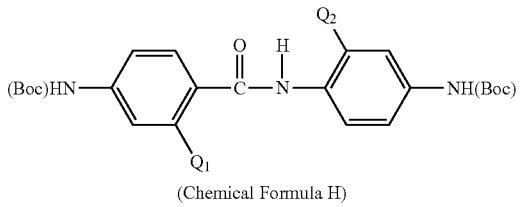

(Chemical Formula H)

Namely, the method for forming an amide group can be divided into a method of reacting carboxylic acid with an amine group and a method of chlorinating carboxylic acid to chlorinated carboxylic acid which has high reactivity with an amine group and then reacting the chlorinated carboxylic acid with the amine group, and as the method for forming an amine group, a method of hydrogenating a nitrile group and a method of hydrogenating an amine group substituted with an amine protecting group can be used.

The present invention provides a polymer obtained from a polymerization reaction by using the diamine compound represented by Chemical Formula 1 as a monomer.

The present invention provides a method for manufacturing the polymer comprising a step of reacting the diamine compound of Chemical Formula 1 with at least one selected from the tetracarboxylic dianhydride of the following Chemical Formula 10, the dicarboxylic acid of Chemical Formula 12 or the dicarboxylic dichloride of Chemical Formula 13:

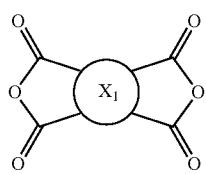

[Chemical Formula 10]

wherein, $X_1$ is a tetravalent organic group containing a $C_{6-30}$ aromatic ring or a $C_{4-30}$ aliphatic ring,

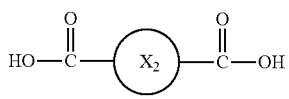

[Chemical Formula 12]

wherein, $X_2$ is a divalent organic group containing a $C_{6-30}$ aromatic ring or a $C_{4-30}$ aliphatic ring,

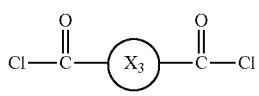

[Chemical Formula 13]

wherein, $X_3$ is a divalent organic group containing a $C_{6-30}$ aromatic ring or a $C_{4-30}$ aliphatic ring.

According to one embodiment, the tetravalent organic group X1 of Chemical Formula 10 may be an intramolecular aromatic, alicyclic or aliphatic tetravalent organic group, or a combination thereof, for example, tetracarboxylic dianhydride in which the aromatic, alicyclic or aliphatic tetravalent organic groups are linked to each other via a crosslink structure. Preferably, it may be acid dianhydride having a monocyclic or polycyclic aromatic group, a monocyclic or polycyclic alicyclic group, or a structure in which at least two thereof are linked to each other via a single bond.

In the Chemical Formula 10, the tetravalent organic group X1 may be a $C_{6-24}$ aromatic tetravalent organic group; an alicyclic tetravalent organic group containing a $C_{3-12}$ cycloalkane structure, or a divalent organic group selected from the group consisting of the structures in which the two or more tetravalent organic group are linked via a single bond, and for example, it may be at least one selected from the tetravalent organic groups containing the structure of the following Chemical Formulas 10a to 10e:

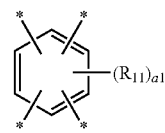

[Chemical Formula 10a]

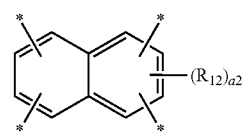

[Chemical Formula 10b]

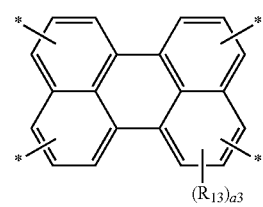

[Chemical Formula 10c]

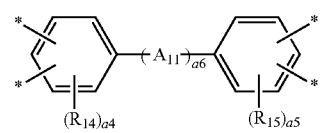

[Chemical Formula 10d]

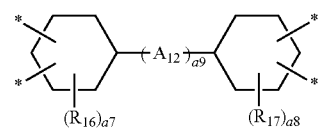

[Chemical Formula 10e]

wherein, $R_{11}$ to $R_{17}$ may be each independently a $C_{1-10}$ alkyl group or a $C_{1-10}$ fluoroalkyl group;

a1 may be an integer of 0 to 2, a2 may be an integer of 0 to 4, a3 may be an integer of 0 to 8, a4 and a5 may be each independently an integer of 0 to 3, a6 and a9 may be each independently an integer of 0 to 3, and a7 and a8 may be each independently an integer of 0 to 9; and $A_{11}$ and $A_{12}$ may be each independently selected from the group consisting of a single bond, —O—, —$CR_{18}R_{19}$—, —C(=O)—, —C(=O)NH—, —S—, —$SO_2$—, a phenylene group and a combination thereof, wherein $R_{18}$ and $R_{19}$ may be each independently selected from the group consisting of a hydrogen atom, a $C_{1-10}$ alkyl group and a $C_{1-10}$ fluoroalkyl group.

More specifically, $X_1$ may be a tetravalent organic group selected from the group consisting of the compounds of the following Chemical Formulas 11a to 11i.

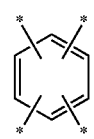

(11a)

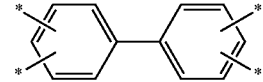

(11b)

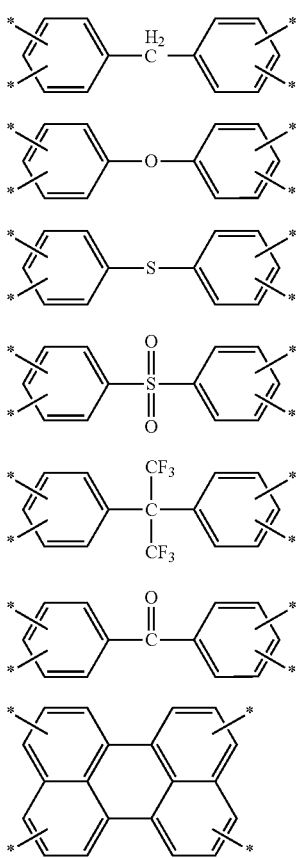

(11c)

(11d)

(11e)

(11f)

(11g)

(11h)

(11i)

At least one hydrogen atom in the tetravalent organic group of the compounds of Chemical Formulas 11a to 11 i may be substituted with a substituent selected from a halogen atom consisting of —F, —Cl, —Br and —I, a hydroxyl group (—OH), a thiol group (—SH), a nitro group (—NO$_2$), a cyano group, a $C_{1-10}$ alkyl group, a $C_{1-4}$ halogenoalkoxyl group, a $C_{1-10}$ halogenoalkyl group, and a $C_{6-30}$ or $C_{6-20}$ aryl group. For example, the halogen atom may be fluoride (—F), the halogenoalkyl may be a $C_{1-10}$ fluoroalkyl containing a fluoride atom selected from a fluoromethyl group, a perfluoroethyl group, a trifluoromethyl group and the like, the alkyl group may be selected from a methyl group, an ethyl group, a propyl group, an isopropyl group, a t-butyl group, a pentyl group and a hexyl group, and the aryl group may be selected from a phenyl group and a naphthalenyl group. More preferably, the substituent may be a fluoride atom and a fluoroalkyl group containing a fluoride atom.

According to one embodiment, in the Chemical Formulas 12 and 13, $X_2$ and $X_3$ may be an aliphatic, alicyclic or aromatic divalent organic group, or a combination thereof, and for example, it may be a divalent organic group in which the aliphatic, alicyclic or aromatic divalent organic groups are directly linked to each other or linked to each other via a crosslink structure.

Specifically, $X_2$ and $X_3$ may be a divalent organic group selected from the group consisting of a $C_{6-24}$ monocyclic or polycyclic aromatic divalent organic group, a $C_{6-18}$ monocyclic or polycyclic alicyclic divalent organic group, or a structure in which at least two of the divalent organic groups are linked via a single bond, and for example, it may be at least one selected from the divalent organic groups containing the structures of the following Chemical Formulas 14a to 14e:

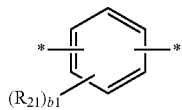

[Chemical Formula 14a]

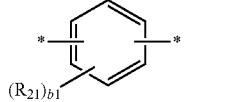

[Chemical Formula 14b]

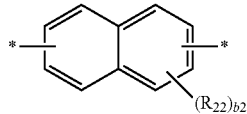

[Chemical Formula 14c]

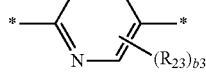

[Chemical Formula 14d]

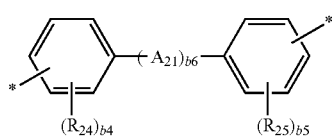

[Chemical Formula 14e]

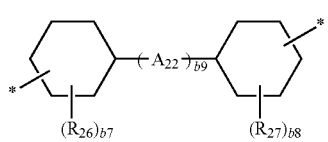

wherein, $R_{21}$ to $R_{27}$ may be each independently selected from the group consisting of a $C_{1-10}$ alkyl group (for example, a methyl group, an ethyl group, a propyl group, an isopropyl group a n-butyl group, a tert-butyl group, a pentyl group and the like), a halogen group, a hydroxyl group, a carboxyl group, a $C_{1-10}$ alkoxyl group (for example, a methoxyl group, an ethoxyl group, a propoxyl group, a tert-butoxyl group and the like) and a $C_{1-10}$ fluoroalkyl group (for example, a trifluoromethyl group and the like), and preferably it may be each independently a methyl group;

$A_{21}$ and $A_{22}$ may be each independently selected from the group consisting of a single bond, —O—, —CR'R''— (wherein, R' and R'' may be each independently selected from the group consisting of a hydrogen group, a $C_{1-10}$ alkyl group (for example, a methyl group, an ethyl group, a propyl group, an isopropyl group a n-butyl group, a tert-butyl group, a pentyl group and the like) and a $C_{1-10}$ fluoroalkyl group (for example, a trifluoromethyl group and the like)), —C(=O)—, —C(=O)O—, —C(=O)NH—, —S—, —SO—, —SO$_2$—, —O[CH$_2$CH$_2$O]y- (y may be an integer of 1 to 44), —NH(C=O)NH—, —NH(C=O)O—, a $C_{6-18}$ monocyclic or polycyclic cycloalkylene group (for example, a cyclohexylene group and the like), a $C_{6-18}$ monocyclic or polycyclic arylene group (for example, a phenylene group, a naphthalene group, a fluorenylene group and the like) and a combination thereof; and b1, b4 and b5 may be each independently an integer of 0 to 4, b2 may be an integer of 0 to 6, b3 may be an integer of 0 to 3, and b6 may be an integer of 0 or 1.

More specifically, $X_2$ and $X_3$ may be each independently a divalent organic group selected from the group consisting of the compounds of the following Chemical Formulas 15a to 15i.

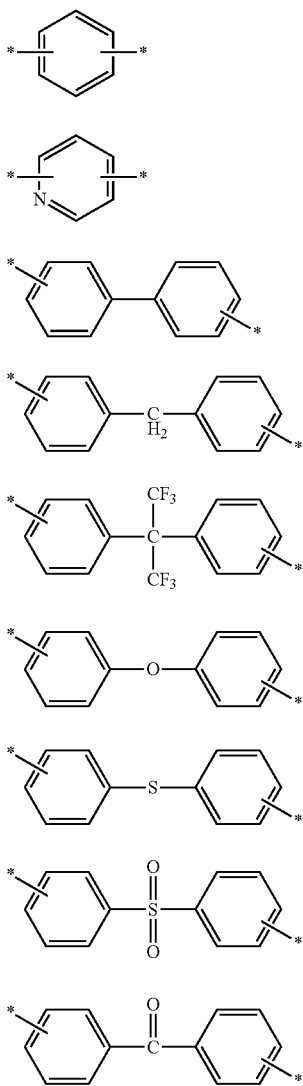

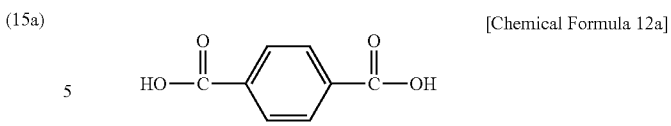

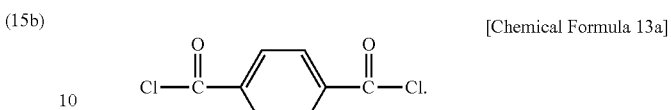

At least one hydrogen atom in the divalent organic group of Chemical Formula 15a to 15i may be substituted with a substituent selected from a halogen atom consisting of —F, —Cl, —Br and —I, a hydroxyl group (—OH), a thiol group (—SH), a nitro group (—$NO_2$), a cyano group, a $C_{1-10}$ alkyl group, a $C_{1-4}$ halogenoalkoxyl group, a $C_{1-10}$ halogenoalkyl group, and a $C_{6-30}$ or $C_{6-20}$ aryl group. For example, the halogen atom may be fluoride (—F), the halogenoalkyl may be a $C_{1-10}$ fluoroalkyl containing a fluoride atom selected from a fluoromethyl group, a perfluoroethyl group, a trifluoromethyl group and the like, the alkyl group may be selected from a methyl group, an ethyl group, a propyl group, an isopropyl group, a t-butyl group, a pentyl group and a hexyl group, and the aryl group may be selected from a phenyl group and a naphthalenyl group. More preferably, the substituent may be a fluoride atom and a fluoroalkyl group containing a fluoride atom.

According to one embodiment, the polymer containing the compound of Chemical Formula 12 or Chemical Formula 13 may surely contain the compound represented by the following Chemical Formula 12a or 13a.

According to one embodiment, polyimide, polyamic acid, polyamide or polyamide-imide may be manufactured by the method for manufacturing a polymer.

According to one embodiment, the present invention may provide a method for manufacturing polyimide comprising the following steps of:

stirring the diamine of Chemical Formula 1;

adding the tetracarboxylic dianhydride of Chemical Formula 10 to the diamine solution followed by reacting thereof to polymerize polyamic acid containing the repeating structure of the following Chemical Formula 16; and imidizing the polyamic acid by dehydrocyclization to manufacture polyimide containing the repeating structure of the following Chemical Formula 17:

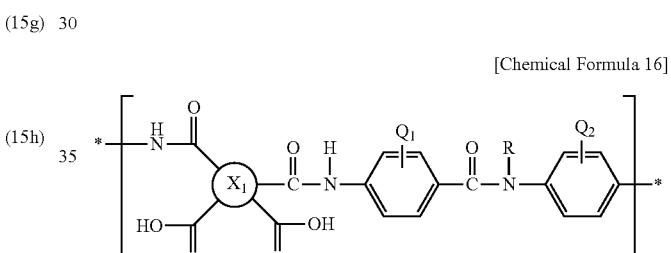

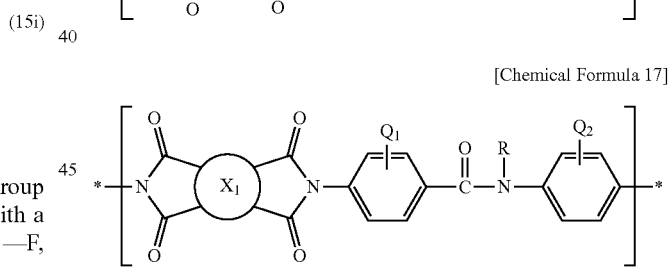

wherein, $X_1$, R, $Q_1$ and $Q_2$ have the same meanings as defined above.

According to one embodiment, the present invention provides a method for manufacturing a polyamide-imide comprising the following steps of:

stirring the diamine of Chemical Formula 1;

adding the tetracarboxylic dianhydride of Chemical Formula 10 to the diamine solution followed by stirring thereof;

adding the dicarboxylic acid of Chemical Formula 12 or the dicarboxylic chloride of Chemical Formula 13 to the solution containing the diamine and the tetracarboxylic dianhydride followed by reacting thereof to manufacture a polyamide-imide precursor containing the repeating structure of Chemical Formula 16 and the repeating structure of Chemical Formula 18 or Chemical Formula 19 together; and imidizing the polyamide-imide precursor:

[Chemical Formula 18]

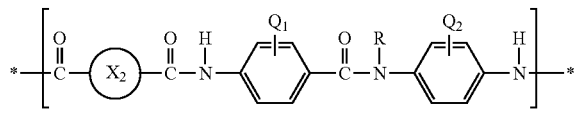

[Chemical Formula 19]

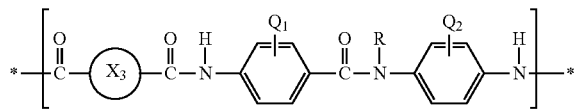

wherein, $X_2$ and $X_3$ have the same meanings as defined above.

According to one embodiment, in the polyamide-imide structure, the tetracarboxylic dianhydride of Chemical Formula 10 and the compound of the Chemical Formula 12 or Chemical Formula 13 may be contained at molar ratio of 1:5 to 2:1. It is preferred to contain the compound of the Chemical Formula 12 or Chemical Formula 13 in a higher amount than the compound of the Chemical Formula 10, and for example, the compound of Chemical Formula 10 and the compound of Chemical Formula 12 or Chemical Formula 13 may be contained at molar ratio of 1:5 to 1:2. Namely, the polyimide repeating structure of Chemical Formula 17 and the polyamide repeating structure of Chemical Formula 18 or Chemical Formula 19 may be contained at molar ratio of 1:5 to 2:1, and preferably, the compounds may be contained at molar ratio of 1:5 to 1:2. A polyamide-imide precursor in which the polyamide repeating structure of Chemical Formula 18 or Chemical Formula 19 is contained in a higher amount than the polyimide repeating structure of Chemical Formula 17 can be manufactured, and by the content ratio, a polyamide-imide film which has excellent transparency while maintaining the mechanical properties and heat resistance can be manufactured.

Further, the present invention provides a method for manufacturing a polyamide containing the repeating structure of Chemical Formula 18 or Chemical Formula 19, which comprises the following steps of:

stirring the diamine of Chemical Formula 1; and adding the dicarboxylic acid of Chemical Formula 12 or the dicarboxylic chloride of Chemical Formula 13 to the diamine solution followed by reacting thereof.

The reaction of the tetracarboxylic dianhydride, the dicarboxylic acid and/or the dicarboxyl chloride with the diamine may be carried out by any common polymerization method for manufacturing polyamic acid, polyamide-imide, polyamide precursor such as solution polymerization. At this time, the total amount of the tetracarboxylic dianhydride, the dicarboxylic acid and/or the dicarboxyl chloride and the amount of the diamine may be mixed at molar ratio of 1:1.1 to 1.1:1 or 1:1.05 to 1.05:1 to obtain preferable molecular weight, mechanical properties and viscosity.

The polymerization reaction may be performed under inert gas or nitrogen atmosphere, and also performed under anhydrous condition.

Further, the polymerization reaction may be performed at a temperature of −20° C. to 60° C., preferably 0° C. to 30° C.

Further, the organic solvent which can be used for the polymerization may be, specifically, selected from the group consisting of ketones such as γ-butyrolactone, 1,3-dimethyl-imidazolidinone, methylethyl ketone, cyclohexanone, cyclopentanone, 4-hydroxy-4-methyl-2-pentanone and the like; aromatic hydrocarbons such as toluene, xylene, tetramethylbenzene and the like; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether and the like; ethyl acetate, butyl acetate, ethyleneglycol monoethyl ether acetate, ethyleneglycol monobutyl ether acetate, diethyleneglycol monoethyl ether acetate, dipropyleneglycol monomethyl ether acetate, ethanol, propanol, ethyleneglycol, propyleneglycol, carbitol, dimethyl acetamide (DMAc), N,N-diethyl acetamide, dimethyl formamide (DMF), diethyl formamide (DEF), N-methyl pyrrolidone (NMP), N-ethyl pyrrolidone (NEP), 1,3-dimethyl-2-imidazolidinone, N,N-dimethylmethoxy acetamide, dimethyl sulfoxide, pyridine, dimethyl sulfone, hexamethyl phosphoramide, tetramethyl urea, N-methyl caprolactam, tetrahydrofuran, m-dioxane, P-dioxane, 1,2-dimethoxyethane, bis(2-methoxyethyl)ether, 1,2-bis(2-methoxyethoxy)ethane, bis[2-(2-methoxyethoxy)]ether, and a mixture thereof.

Preferably, the solvent may be a sulfoxide-based solvent such as dimethyl sulfoxide, diethyl sulfoxide and the like; a formamide-based solvent such as N,N-dimethyl formamide, N,N-diethyl formamide and the like; an acetamide-based solvent such as N,N-dimethyl acetamide, N,N-diethyl acetamide and the like; a pyrrolidone-based solvent such as N-methyl-2-pyrrolidone, N-ethyl pyrrolidone (NEP), N-vinyl-2-pyrrolidone and the like; a phenol-based solvent such as phenol, o-, m- or p-cresol, xylenol, halogenated phenol, catechol and the like; or hexamethyl phosphoramide, y-butyrolactone and the like. More preferably, the organic solvent may be a solvent having the partition coefficient (LogP value) at 25° C. as a positive value and the boiling point of 180° C. or lower, and more specifically the solvent may have the partition coefficient (LogP value) of 0.01 to 3, 0.01 to 2, or 0.01 to 1. The partition coefficient may be calculated by using an ACD/LogP module of ACD/Percepta platform (ACD/Labs), and the ACD/LogP module uses algorithm based on Quantitative Structure-Property Relationship (QSPR) methodology which uses a 2D structure of a molecule.

The solvent with the positive partition coefficient (LogP) may be, for example, at least one selected from N,N-diethyl formamide, N,N-diethyl acetamide, N-ethyl pyrrolidone (NEP) and the like, and the solvent may be used alone or as a mixture thereof, but not limited thereto. An aromatic hydrocarbon such as xylene and toluene may be further used, and in order to accelerate dissolution of the polymer, an alkali metal salt or alkali earth metal salt may be further added to the solvent in an amount of about 50 wt % or less, based on the total amount of the solvent.

The polymer composition or the polymer precursor composition manufactured by the method mentioned above may contain the solid component in such an amount that the composition has an appropriate viscosity considering its film formation processability such as coatability. According to one embodiment, the content of the composition may be controlled to have the total content of the polymer of 5 to 25 wt %, preferably 5 to 20 wt %, more preferably 5 to 20 wt % or 5 to 15 wt %.

Further, the content of the composition may be controlled such that the polymer composition or the polymer precursor composition has the viscosity of 500 cP or higher or 1,000 cP or higher, preferably 3,000 cP or higher, and the viscosity of the composition may be controlled to 30,000 cP or lower or 20,000 cP or lower, preferably 18,000 cP or lower or 15,000 cP or lower. If the viscosity of the composition is lower than 500 cP or higher than 30,000 cP, optical properties of the film may be deteriorated due to bubble formation during the process and bad surface profile.

Further, the polymer according to the present invention, for example, polyamic acid, polyimide, polyamide or polyamide-imide may have a weight average molecular weight of 10,000 to 200,000 g/mol, 20,000 to 100,000 g/mol or 30,000 to 100,000 g/mol.

Further, the polymer according to the present invention may have a molecular weight distribution (Mw/Mn) of 1.1 to 2.5, preferably. If the weight average molecular weight or molecular weight distribution of the polymer is out of the range defined above, there may be a difficulty in forming the film or there is a risk that the characteristics of the polyamide-imide-based film such as transmittance, heat resistance and mechanical properties may be deteriorated.

The polymer composition may be in the form of a solution dissolved in an organic solvent, and in this case, for example, when the polyamide-imide precursor or polyamic acid is synthesized in the organic solvent, the solution may be the reaction solution thus obtained itself or a solution obtained by diluting the reaction solution with another solvent. Further, when the polyamide-imide precursor or polyamic acid is obtained as powder, the solution may be a solution obtained by dissolving the powder in an organic solvent.

Further, when preparing the solution by dissolving the polymer powder in an organic solvent, the reaction may be conducted by heating at a temperature of, preferably, 20° C. to 150° C., more preferably, 20° C. to 80° C.

The polymer manufactured with the diamine compound according to the present invention may be, for example, polyamic acid, polyimide, polyamide-imide or polyamide, and the absorbance thereof at 308 nm may be in a range from 0.1 to 0.9 at 1 cm of the measured thickness of the solution.

The diamine of the present invention has a very rigid molecular structure in which two benzene rings are linked to each other via an amide group, and therefore, it can exhibit excellent heat resistance. Further, by substituting the benzene ring with a substituent having high electronegativity, for example, fluoroalkyl, the rotation of the benzene ring can be inhibited, and therefore its rigid structure can be maintained. Accordingly, a polymer which can exhibit a physical characteristic of effectively maintaining the heat resistance can be provided. Further, because the substituent reduces the CT-complex caused by the intermolecular charge transfer, and therefore, the transmittance of the light between 400 nm to 500 nm is increased, a polymer which can exhibit low yellowness index characteristic can be provided.

Further, the amide bond formed between the benzene rings can increase the packing density by an intermolecular bonding through hydrogen bond, thereby enhancing the heat resistance. However, too high packing density caused by high intermolecular hydrogen bonding may deteriorate the transparency finally. The diamine structure according to the present invention can inhibit too high packing density by forming a substituent with high electronegativity on the benzene ring, thereby forming a polymer which exhibits the colorless transparent characteristic while maintaining excellent heat resistance, which is formed from the rigid structure by the amide group and the benzene structure.

The diamine structure according to the present invention has high absorbance at 308 nm by the amide bond formed in the structure, and therefore, during a lase release process after a display panel process, effective release is possible with only low energy, i.e., energy density of 180 mJ/cm$^2$.

The diamine structure according to the present invention is advantageous to enhance the transparency and has the amide bond which can be degraded by light. Thus, it can be used to a monomer for photo-alignment which can be degraded by light and can exhibit the orientation.

According to one embodiment, the film manufactured with the polymer may have a thickness of 5 μm to 50 μm, and the haze of 2 or less, preferably 1 or less, or 0.9 or less, more preferably 0.7 or less. Further, it may be a colorless transparent polymer film having the yellowness index (YI) of about 20 or less, preferably about 18 or less, more preferably about 15 or less. The film can exhibit markedly improved transparency and optical properties due to its excellent light transmittance and yellowness index.

Further, the polymer film may be an anisotropic film having an in-plane retardation ($R_{in}$) of about 0 to about 100 nm and a thickness retardation ($R_{th}$) of at least about 200 nm, or an in-plane retardation ($R_{in}$) of about 0 to about 70 nm and a thickness retardation ($R_{th}$) of at least about 300 nm.

Further, the polymer film may have the coefficient of thermal expansion (CTE) in a range from 0 ppm/° C. to 20 ppm/° C., preferably from 0 ppm/° C. to 15 ppm/°, more preferably from 0 ppm/° C. to 10 ppm/° C. after performing a heating and cooling process n+1 times (n is an integer equal to or greater than 0) at a temperature ranging from 100° C. to 300° C.

Further, the polymer film may have the E (%) calculated according to the following Formula 1 of −20≤E≤0 and the K (%) calculated according to Formula 2 of 0≤K≤20 when calculating the average value of the coefficient of thermal expansion (CTE) measured by repeating a heating and cooling process 2m+1 times (m is an integer of 1 to 3) at a temperature ranging from 50° C. to 200° C.

(Minimum CTE value−Average CTE value)/Average CTE value×100=$E$    [Formula 1]

(Maximum CTE value−Average CTE value)/Average CTE value×100=$K$    [Formula 2]

According to one embodiment, the coefficient of thermal expansion of the polymer film at a temperature ranging from 50° C. to 200° C. may be in a range from 0 ppm/° C. to 50 ppm/° C., preferably from 0 ppm/° C. to 20 ppm/° C.

In the present invention, the range of the E (%) calculated according to the Formula 1 and the K (%) calculated according to Formula 2, i.e., the range of E-K may be defined as a range of CTE hysteresis.

If the range of CTE hysteresis is more than ±20%, i.e., if the E is less than −20% or the K is more than 20%, during a following process, for example, loading a thin film transistor (TFT) (TFT array), the size change of a polyimide substrate according to the change of a process temperature becomes very big and the degree of the change fluctuates. Accordingly, it is difficult to perform alignment by predicting the size change of a substrate at the corresponding process.

Thus, in another embodiment of the present invention, an article comprising the polymer is provided.

The article maybe a film, a fiber, a coating material, an adhesive and the like, but not limited thereto. The article may be formed by a dry/wet method, a dry method, a wet method and the like using a composite composition of the copolymer and inorganic particles, but not limited thereto. Specifically, as described above, the article may be an optical film, and in this case, the composition comprising the polymer may be easily manufactured by being applied on a substrate through a spin coating method followed by being dried and cured The polymer polymerized by using the diamine according to the present invention as a monomer, for example, polyamic acid, polyimide or polyamide-imide can have excellent colorless transparent characteristic while maintaining characteristics such as heat resistance, mechanical strength and the like due to its rigid structure. Thus, it can be used in various fields such as a substrate for a device, a cover substrate for a display, an optical film, an integrated circuit (IC) package, an adhesive film, a multi-layer flexible printed circuit (FPC), a tape, a touch panel, a protection film for an optical disk and the like, and in particular, it may be suitable for the cover substrate for a display.

According to another embodiment of the present invention, a display device comprising the article is provided. Specifically, the display device may be a liquid crystal display device (LCD), an organic light emitting diode (OLED) and the like, but not limited thereto.

MODE FOR INVENTION

The present invention will be explained in detail with reference to the following examples, including test examples. However, these examples are provided for illustrative purposes only and are not intended to limit the scope of the invention.

EXAMPLE

Example 1: Manufacture of Novel Diamine (1)

A diamine compound having a novel structure was prepared according to the following method.

Preparation of 4-Nitro-2-(trifluoromethyl)benzoic acid (B)

2-Bromo-5-nitrobenzo trifluoride (20 g, 0.111 mol) and CuCN (12 g, 0.134 mol) were dissolved in a 250 ml 3-neck reaction flask containing DMF (90 ml), respectively. Then, the solution was refluxed at 160° C. for 18 hours at nitrogen atmosphere to synthesize 2-cyano-5-nitrobenzotrifluoride (A).

Then, the reactant was cooled to room temperature and homogeneously mixed with a pre-made workup solution (FeCl$_3$ 50 g, conc. HCl 30 ml, DI water 500 ml). The mixture was extracted with ethyl acetate and subjected to fractional washing with 10% (v/v) aqueous HCl solution followed by evaporating the ethyl acetated by using a rotary evaporator. Finally, dark brown liquid was obtained, and the solvent remained in the brown liquid was evaporated and removed in a 80° C. vacuum oven to obtain 2-cyano-5-nitrobenzotrifluoride.

First, NaOH (5.88 g, 0.147 mol) was dissolved in ethanol/DI water (1:1) 400 ml in a 3-neck reaction flask, and then the 2-cyano-5-nitrobenzotrifluoride (9.34 g, 0.0368 mol) synthesized above was added thereto. The resulting solution was refluxed at 80° C. overnight to synthesize 4-nitro-2-(trifluoromethyl)benzoic acid (B). After the reaction, the solution was cooled again to room temperature and then ethanol was evaporated followed by neutralizing thereof with 1N aqueous HCl solution. Then, the precipitated solid was filtered through a filter paper. The solid was washed with a small amount of DI water to obtain 4-nitro-2-(trifluoromethyl)benzoic acid.

Step 1: Preparation of 4-Nitro-2-(trifluoromethyl) phenyl 4-Nitro-2-(trifluoromethyl)benzanilide (D)

The 4-nitro-2-(trifluoromethyl)benzoic acid (23.51 g, 0.1 mol) (B) manufactured above and thionyl chloride (17.85 g, 0.15 mol) were put into a 3-neck reaction flask containing 250 ml of chloroform and heated thereof at 60° C. for 2 hours. Then, the resulting solution was cooled to room temperature and the chloroform and thionyl chloride were evaporated by using a rotary evaporator. Then, DMAc 300 ml and 2-amino-5-nitrobenzotrifluoride (20.61 g, 0.1 mol) (C) were added thereto and reacted overnight to synthesize 4-nitro-2-(trifluoromethyl)phenyl 4-nitro-2-(trifluoromethyl)benzanilide (D). After completing the reaction, the compound was precipitated in 1 L of DI water and filtered, and then the filtered compound was dissolved again in 1 L of ethyl acetate (EA) followed by extracting thereof with DI water. Then, the organic layer was dried with MgSO$_4$ and the EA was evaporated. Then, recrystallization was performed in ethanol to obtain 4-nitro-2-(trifluoromethyl)phenyl 4-nitro-2-(trifluoromethyl)benzanilide having a pure solid state.

Step 2: Preparation of Diamine Compound

4-Nitro-2-(trifluoromethyl)phenyl 4-nitro-2-(trifluoromethyl)benzanilide (42.32 g, 0.1 mol) (D) prepared in the step 1 and Tin(II) chloride (189.6 g, 1 mol), HCl 5 ml were put into a 3-neck reaction flask together with 400 ml of absolute ethanol and then refluxed at 80° C. for 1 hour. After completing the reaction, the reacted material was diluted with 500 ml of DI water. Then, a pre-make K$_2$CO$_3$ saturated aqueous solution was gradually added thereto and stirred for hydrogenating the 4-nitro-2-(trifluoromethyl)phenyl 4-nitro-2-(trifluoromethyl)benzanilide (D), so as to synthesize the diamine compound of the following Chemical Formula 1a-1. When pH reached to 7 to 8, the addition was stopped and the resulting solution was extracted with a large amount of ethyl acetate (EA) and DI water to separate the synthesized diamine compound through the organic layer. Then, the organic layer was also dried with MgSO$_4$ and the EA was evaporated. Then, recrystallization was performed in ethanol to finally obtain a diamine compound having a crystalline solid state.

The above reaction steps were shown in the following Reaction Formula I.

[Reaction Formula I]

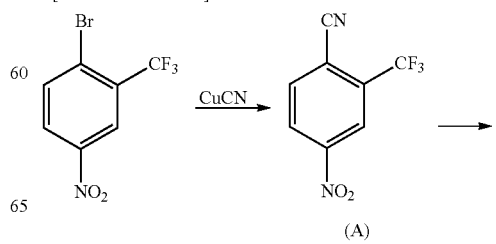

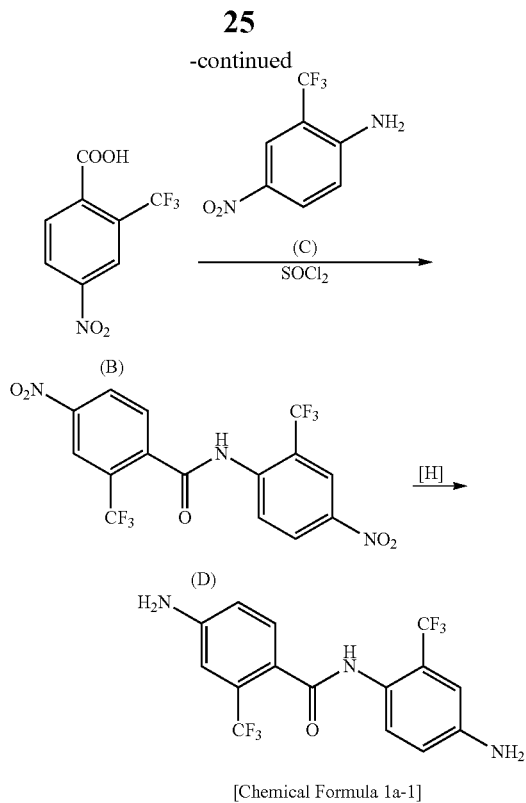

[Chemical Formula 1a-1]

Figure 2:
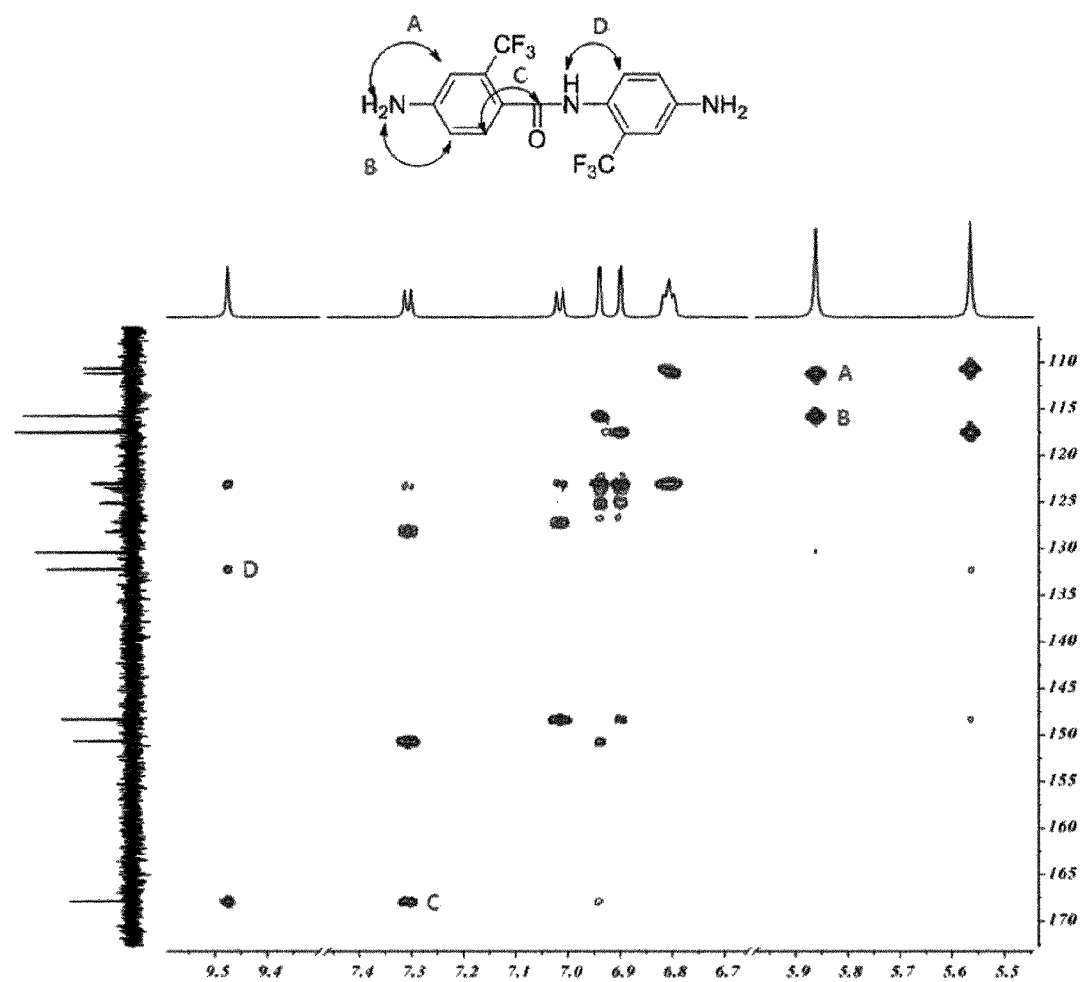
FIG. 2 is the result of $^1$H-$^{13}$C analysis of the diamine compound manufactured according to Example 1 of the present invention.

The results of measuring $^1$H NMR and $^1$H-$^{13}$C NMR of the compound synthesized above were shown in FIG. 1 and FIG. 2, and the results of $^1$H NMR and $^1$H-$^{13}$C NMR showed that the synthesized compound has the structure of the diamine compound of Chemical Formula 1a-1.

Example 2: Preparation of Novel Diamine Compound(2)

Preparation of 2-Trifluoromethyl-4-(tert-butoxycarbonylamino)benzoyl chloride (F)

2-Trifluoromethyl-4-(tert-butoxycarbonylamino) benzoyl chloride (F) was synthesized by the method of the following Reaction Formula A.

[Reaction Formula A]

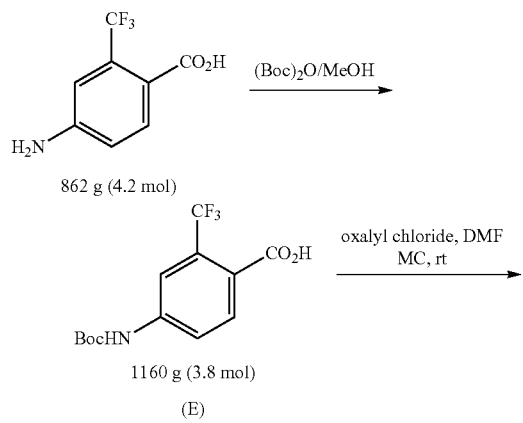

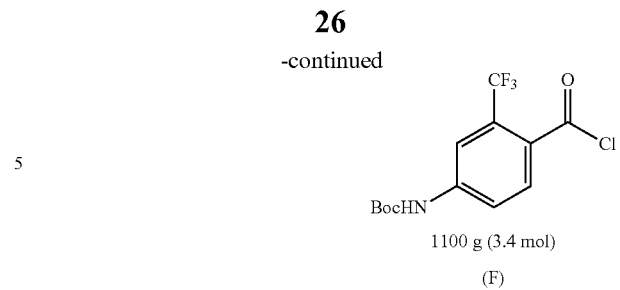

Specifically, after dissolving 4-amino-2-(trifluoromethyl) benzoic Acid 862 g (4.20 mol) in 1 L of absolute methanol at nitrogen atmosphere, 935 g (4.29 mol) of di-tert-butyl dicarbonate was added thereto and stirred overnight at a reflux condition. After completing the stirring, the methanol was partly evaporated by using a rotary evaporator. Then, the remained solid was intactly filtered and recrystallized again in hot absolute methanol to obtain 1160 g of 2-trifluoromethyl-4-(tert-butoxycarbonylamino)benzoic Acid (E) in pure solid state (Yield: 90.4%).

After homogeneously dispersing 1160 g (3.80 mol) of 2-trifluoromethyl-4-(tert-butoxycarbonylamino)benzoic Acid (E) synthesized above in 1 L of methylene chloride at nitrogen atmosphere, 2 drops of N,N-dimethyl formamide were added thereto. Then, 579 g (4.56 mol) of oxalyl chloride was added to the solution dropwise and reacted at room temperature for 6 hours. After completing the reaction, the solution was stood until bubbles were not formed anymore and the solution kept transparent, and then the oxalyl chloride and the methylene chloride were evaporated by using a rotary evaporator. Then, the remained oxalyl chloride and methylene chloride were completely evaporated in a vacuum oven to obtain 1100 g of 2-trifluoromethyl-4-(tert-butoxycarbonylamino)benzoyl chloride (F) in solid state (Yield: 89.4%)

Preparation of N4-(tert-Butoxycarbonyl)-2-trifluoromethyl-1,4-phenylenediamine (G)

N4-(tert-Butoxycarbonyl)-2-trifluoromethyl-1,4-phenylenediamine (G) was prepared by the method of the following Reaction Formula B.

[Reaction Formula B]

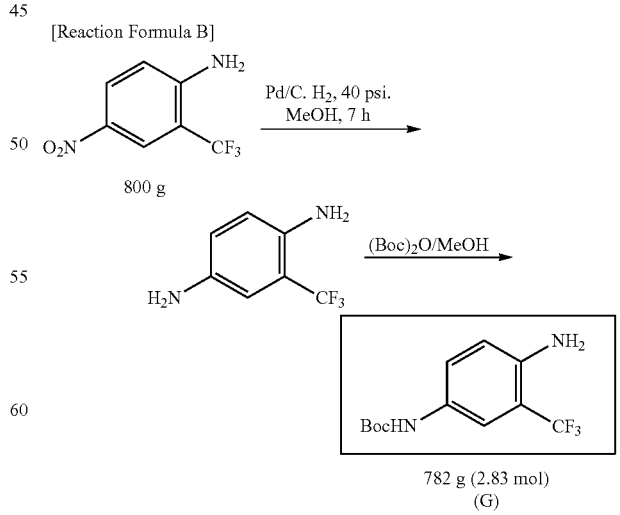

Specifically, 800 g (3.88 mol) of 2-amino-5-nitrobenzotrifluoride was added to 1 L of absolute methanol and dissolved at nitrogen atmosphere. Then, 60 g of a palladium catalyst (10% on carbon) was homogeneously dispersed in the solution, and H₂ gas was blown into the solution through a nozzle at a pressure of 40 psi for 7 hours. After completing the reaction, the nozzle was removed and then 864 g (3.96 mol) of di-tert-butyl dicarbonate was added to the reacted solution and stirred at a reflux condition overnight. After completing the stirring, the methanol was evaporated by using a rotary evaporator and recrystallized with hexane to obtain 782 g of N4-(tert-Butoxycarbonyl)-2-trifluoromethyl-1,4-phenylenediamine (G) in pure solid state (Yield: 72.9%).

Step 1: Preparation of 4-tert-butoxycarbonylamino-2-trifluoromethylphenyl 4-tert-butoxycarbonylamino-2-trifluoromethylbenzanilide (H)

After dissolving N4-(tert-butoxycarbonyl)-2-trifluoromethyl-1,4-phenylenediamine (G) 938 g (3.40 mol) synthesized above in 1 L of tetrahydrofuran, 269 g (3.40 mol) of pyridine was added thereto. Then, while maintaining the reaction temperature at 0° C., 1100 g (3.40 mol) of 2-trifluoromethyl-4-(tertbutoxycarbonylamino)benzoyl chloride (F) was added to the resulting solution into three equal portions. After completing the addition, the reaction temperature was slowly increased to room temperature and the resulting solution was stirred for 2 hours. After completing the reaction, the solution was extracted with ethyl acetate/DI water to separate the organic layer. Then, the layer was dried with MgSO₄ and the ethyl acetate was evaporated by using a rotary evaporator. The remained solid was recrystallized in hot absolute ethanol to obtain 1116 g of 4-tert-butoxycarbonylamino-2-trifluoromethylphenyl 4-tert-butoxycarbonylamino-2-trifluoromethylbenzanilide (H) in pure solid state (Yield: 58.2%).

Step 2: Manufacture of Diamine Compound

After homogeneously dispersing the recrystallized 4-tert-butoxycarbonylamino-2-trifluoromethylphenyl 4-tert-butoxycarbonylamino-2-trifluoromethylbenzanilide (H) 1116 g (1.98 mol) in 1 L of methylene chloride, 5 ml of trifluoroacetic acid was added thereto and stirred for 3 hours. Then, the resulting solution was filtered and recrystallized in hot absolute ethanol to obtain 500 g of the diamine compound of Chemical Formula 1a-1 in pure crystalline solid state (Yield: 69.7%).

The above reaction steps were shown in the following Reaction Formula II.

[Reation Formula II]

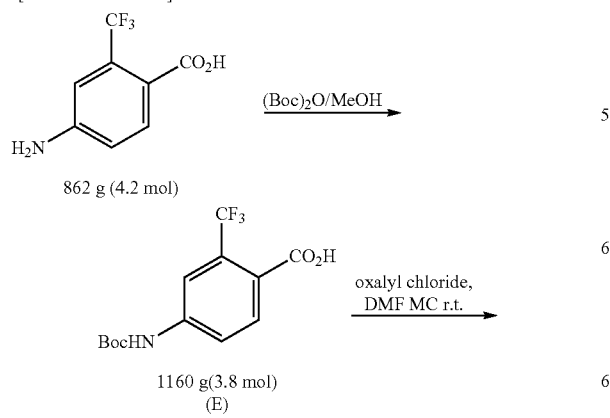

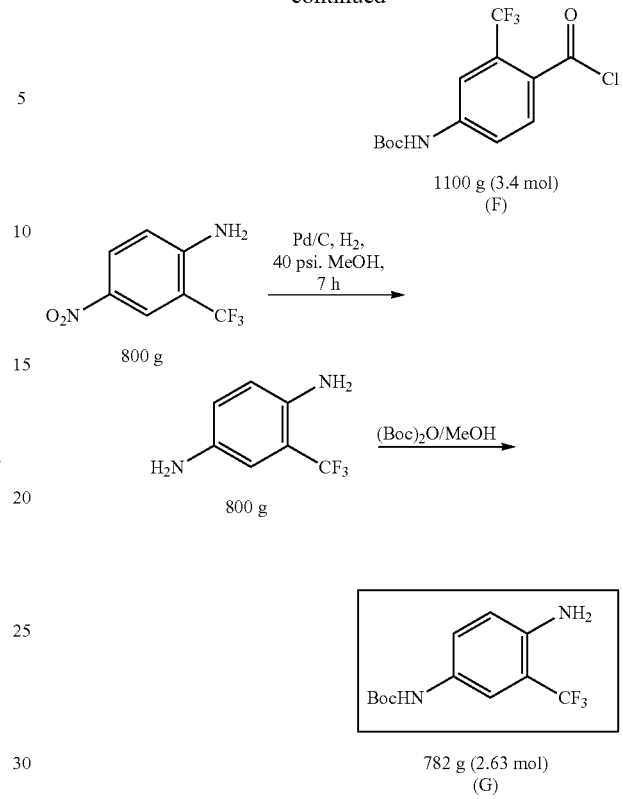

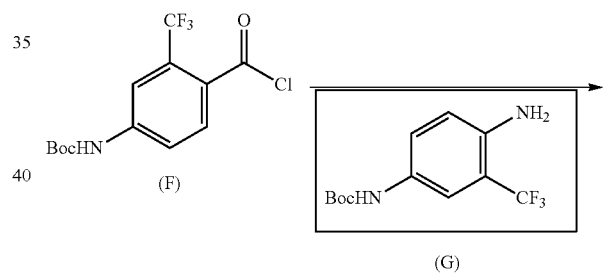

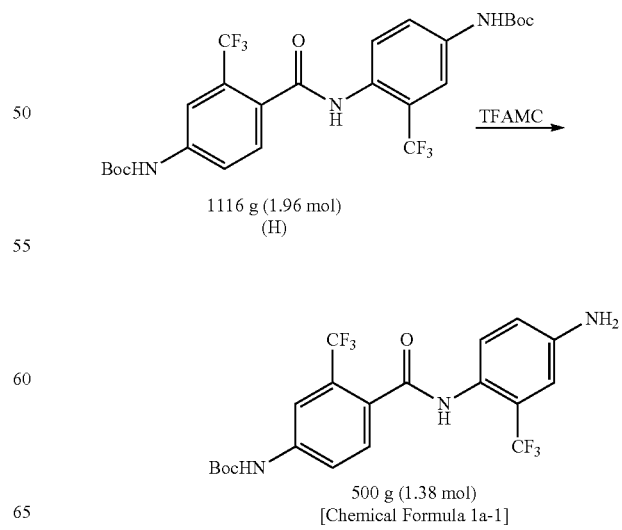

Figure 3:
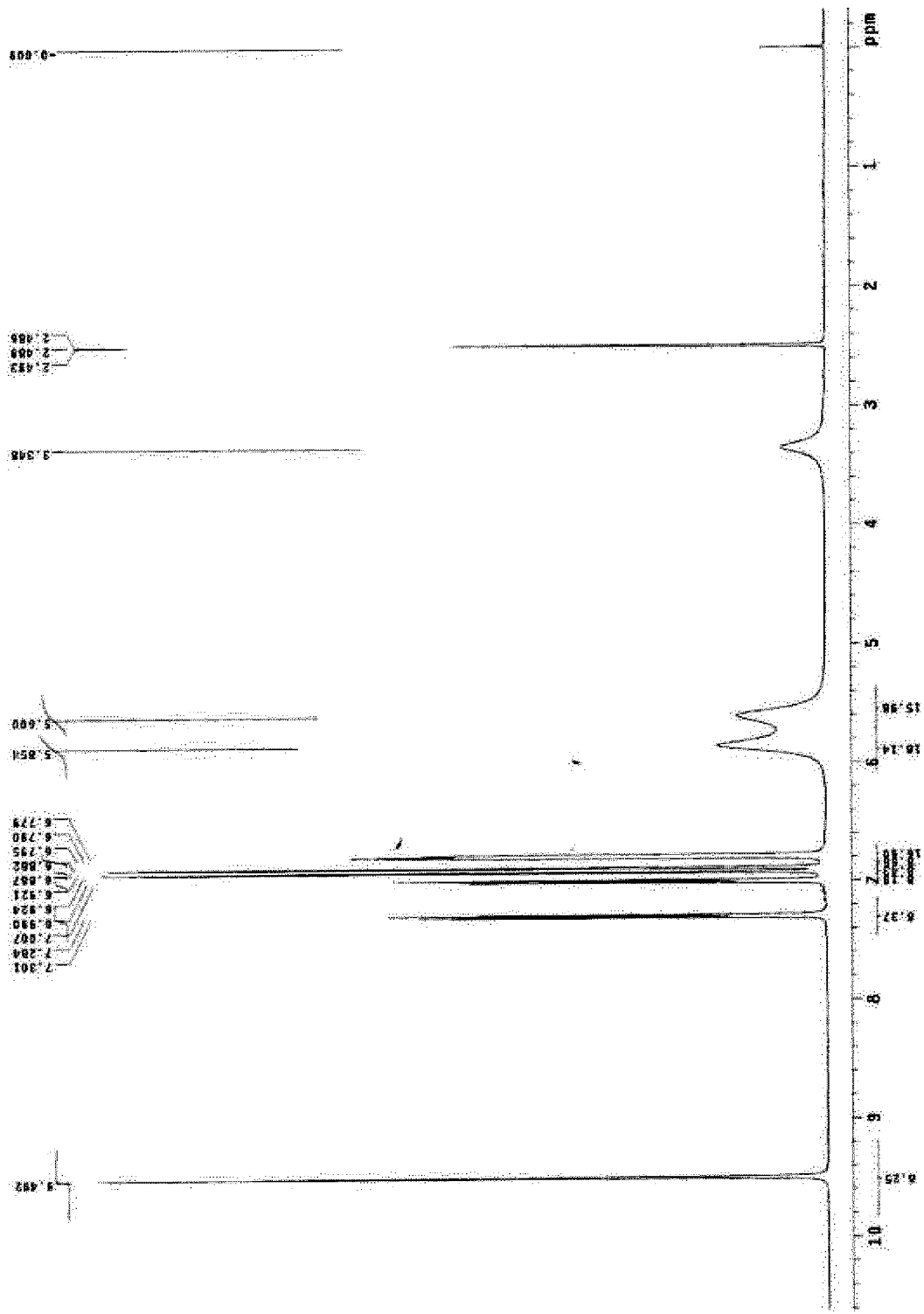
FIG. 3 is the result of $^1$H NMR analysis of the diamine compound manufactured according to Example 2 of the present invention.

The results of measuring $^1$H NMR of the compound synthesized above were shown in FIG. 3, and the results of $^1$H NMR showed that the synthesized compound has the structure of the diamine compound of Chemical Formula 1a-1.

Test Example 1: HPLC Measurement

Figure 4:
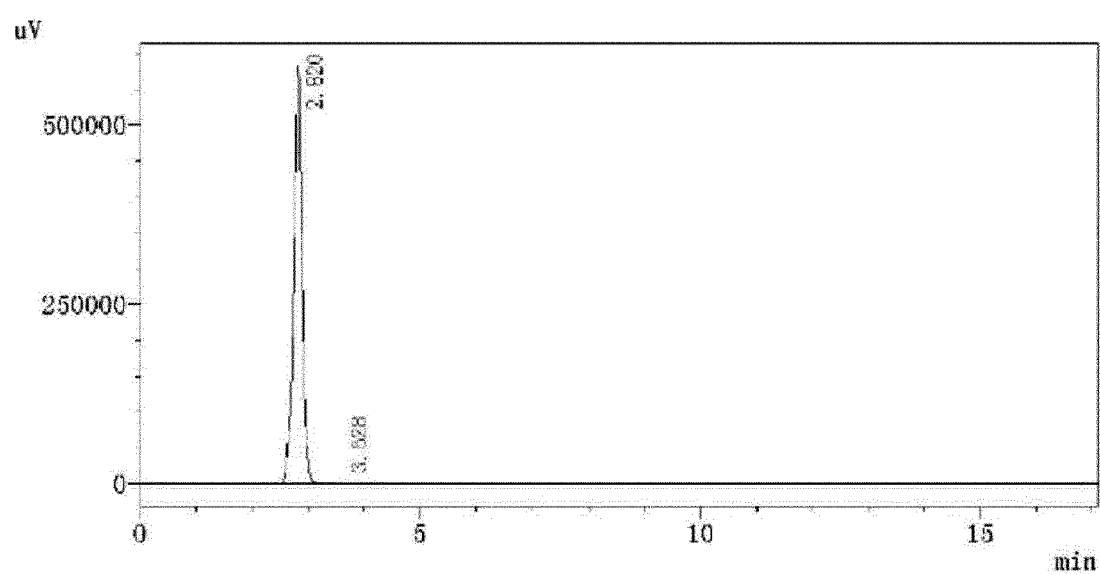
FIG. 4 is the result of HPLC analysis of the diamine compound manufactured according to Example 1 of the present invention.
Figure 5:
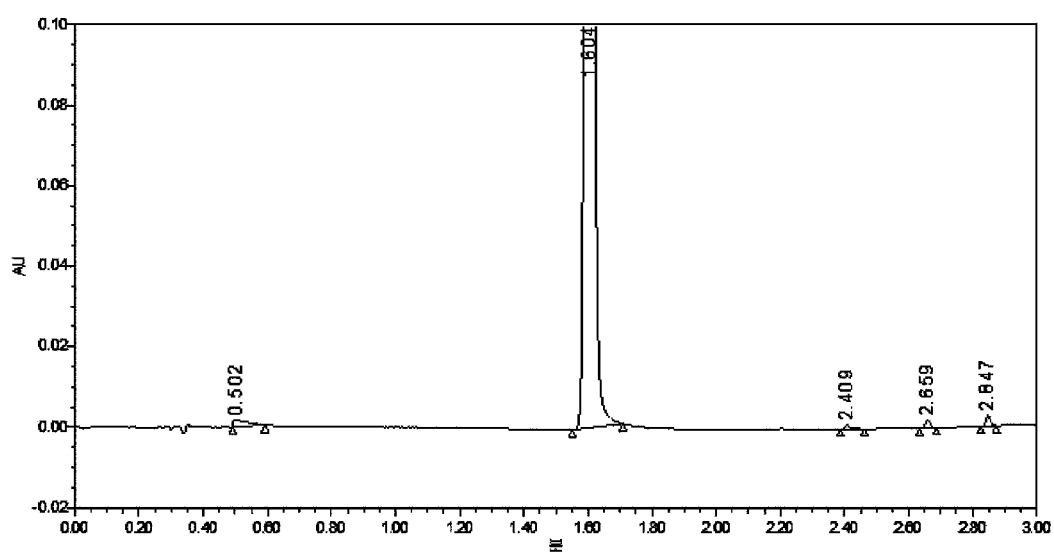
FIG. 5 is the result of HPLC analysis of the diamine compound manufactured according to Example 2 of the present invention.

The diamine compounds manufactured in Example 1 and Example 2 were diluted in THF at a concentration of 1.5 mg/ml, and HPLC was measured at 255 nm wavelength at the flow rate of 0.4 mL/min. At this time, as an eluent, MeOH:$H_2O$ (100 (v/v %):100 (v/v %)) was used. The results were shown in FIG. 4 (Example 1) and FIG. 5 (Example 2).

The results of measuring HPLC of the diamine compound manufactured in Example 1 were listed in the following Table 1.

TABLE 1

| Example 1 | Retention time | Area | Height | Area % | Height % |
|---|---|---|---|---|---|
| 1 | 2.820 | 6034287 | 580852 | 99.865 | 99.941 |
| 2 | 3.628 | 8140 | 344 | 0.135 | 0.059 |
| Total |  | 6042427 | 581196 | 100.00 | 100.00 |

The results of measuring HPLC of the diamine compound manufactured in Example 2 were listed in the following Table 2.

TABLE 2

| Example 2 | Retention time | Area | Height | Area % | Height % |
|---|---|---|---|---|---|
| 1 | 0.502 | 4644 | 0.35 | 1488 | 6.050 |
| 2 | 1.604 | 1331736 | 99.22 | 997729 | 9.501 |
| 3 | 2.409 | 1393 | 0.10 | 915 | 4.550 |
| 4 | 2.659 | 1938 | 0.14 | 1859 | 3.150 |
| 5 | 2.847 | 2490 | 0.19 | 2575 | 2.850 |

From the results of measuring HPLC of Table 1 and Table 2, it can be found that the diamine compounds synthesized in Example 1 and Example 2 were synthesized in a purity of 99.8% or more.

Example 3

14 g of the diamine compound of Chemical Formula 1a-1 (4-amino-N-[4-amino-2[trifluoromethyl]phenyl-2-[trifluoromethyl]benzamide], BTFMADABA) manufactured in Example 1 was dissolved in 50 g of anhydrous diethylacetamide (DEAc) for 20 min at nitrogen atmosphere. BTFMADABA/DEAc solution manufactured by dissolving 9.26 g of 4,4'-Biphthalic dianhydride (BPDA) in 40 g of anhydrous DEAc was added to the BTFMADABA/DEAc solution thus obtained and then reacted at 25° C. for 2 hours followed by reacting at 45° C. for 24 hours. DEAc was added to the reacted solution thus obtained to control the wt % of the solid so as to make the viscosity of the reacted solution 10,000 cP, and then homogeneously mixed the resulting solution for 24 hours to manufacture a polyimide precursor solution.

The manufactured polyimide precursor solution was spin coated on a glass substrate to a thickness of 20 μm. The glass substrate coated with the polyimide precursor solution was put into an oven and heated at a rate of 2° C./min followed by performing a curing process at 80° C. for 15 min, at 150° C. for 30 min, at 220° C. for 30 min and at 380° C. for 1 hour. After completing the curing process, the glass substrate was immersed in water to detach the film formed on the substrate, and then the film was dried in an oven at 100° C. to manufacture a polyimide film containing the structure of the following Chemical Formula 20.

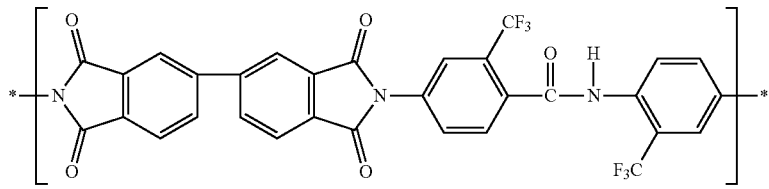

[Chemical Formula 20]

Comparative Example 1

12 g of 4,4'-Biphthalic dianhydride BPDA was dissolved in 50 g of anhydrous diethylacetamide (DEAc) for 20 min at nitrogen atmosphere. DABA/DEAc solution manufactured by dissolving 9.26 g of 4-amino-N-(4-aminophenyl)benzamide (DABA) in anhydrous 40 g of DEAc was added to the BPDA/DEAc solution thus obtained and then reacted at 25° C. for 2 hours followed by reacting at 45° C. for 24 hours. DEAc was added to the reacted solution thus obtained to control the wt % of the solid so as to make the viscosity of the reacted solution 10,000 cP, and then homogeneously mixed the resulting solution for 24 hours to manufacture a polyimide precursor solution.

The manufactured polyimide precursor solution was spin coated on a glass substrate to a thickness of 20 μm. The glass substrate coated with the polyimide precursor solution was put into an oven and heated at a rate of 2° C./min followed by performing a curing process at 80° C. for 15 min, at 150° C. for 30 min, at 220° C. for 30 min and at 380° C. for 1 hour. After completing the curing process, the glass substrate was immersed in water to detach the film formed on the substrate, and then the film was dried in an oven at 100° C. to manufacture a polyimide film containing the structure of the following Chemical Formula 21.

[Chemical Formula 21]

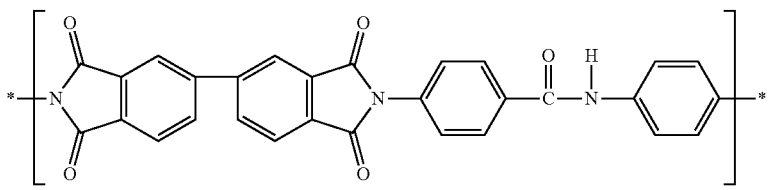

Test Example 2

For the polyimide films manufactured in Example 3 and Comparative Example 1, optical properties of the films such as transmittance, yellowness index and coefficient of thermal expansion were measured by the following method, respectively. The results of the measurement were listed in Table 3.

The transmittance was measured according to JIS K 7105 by using a transmittance meter (Model name: HR-100, manufactured by Murakami Color Research Laboratory) at 450 nm.

The yellowness index (YI) was measured by using a color-difference meter (Color Eye 7000A).

The haze was measured by using Haze Meter HM-150 according to the method of ASTM D1003.

The Tg and the coefficient of thermal expansion (CTE) were measured by using TMA (Q400 of TA Instruments). Specifically, the film was prepared in the size of 5×20 mm, and a sample was loaded thereon using an accessory. The actual measured film length was equally set to 16 mm. The force pulling the film was set to 0.02 N. The first heating process was performed at a temperature ranging from 100° C. to 300° C. at heating rate of 4° C./min, and then the change aspect on the thermal expansion when the film was cooled at a temperature ranging from 300° C. to 100° C. at cooling rate of 4° C./min was measured.

The force pulling the film was set to 0.02 N, and then the change aspect on the thermal expansion was measured after repeating the heating process performed at a temperature ranging from 50° C. to 200° C. at heating rate of 4° C./min and the cooling process performed at a temperature ranging from 200° C. to 50° C. at heating rate of 4° C./min three times. From the result values of the CTE, an average value of the measured CTE values was measured, and the E value and the K value were calculated according to the following Formula 1 and Formula 2.

(Minimum CTE value−Average CTE value)/Average CTE value 100=$E$ [Formula 1]

(Maximum CTE value−Average CTE value)/Average CTE value×100=$K$ [Formula 2]

TABLE 3

|  |  | Example 3 | Comparative Example 1 |
|---|---|---|---|
| Thickness (μm) |  | 9.9 | 9.8 |
| YI |  | 12 | 44 |
| T % @ 450 nm |  | 65 | 40 |
| Haze |  | 0.33 | 0.45 |
| CTE 1$^{st}$ cooling (100-300° C.) |  | 5.7 | −1.3 |
| CTE | 1st | 3.60 | −0.65 |
| (50-200° C.) | 2nd | 4.64 | −0.86 |
|  | 3rd | 4.87 | −0.79 |

TABLE 3-continued

|  | Example 3 | Comparative Example 1 |
|---|---|---|
| E | 17.6 | −14.4 |
| K | 11.4 | 3.9 |
| Tg (° C.) ~430° C. | N.D. | N.D. |

As shown in the Table 3, it can be found that the film comprising the diamine compound according to the present invention has remarkably excellent yellowness index and transmittance characteristics compared to the polyimide film of Comparative Example 1, and also has excellent thermal expansion characteristic.

Although specific embodiments of the present invention are described in detail as described above, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A transparent film for a flexible substrate of a display device comprising a polymer comprising:
at least one repeating unit of Chemical Formula 16:

[Chemical Formula 16]

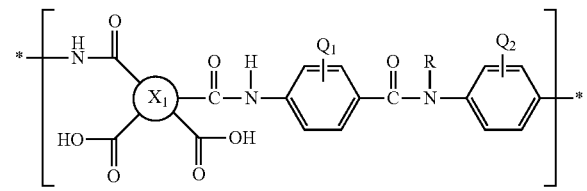

wherein, $Q_1$ and $Q_2$ are each independently selected from a fluoride atom (F), a C1-5 fluoroalkyl group, and a cyano group (CN); and
R is a hydrogen atom, a C1-10 alkyl group or a C6-30 aryl group,
wherein, $X_1$ is at least one tetravalent organic group selected from the compounds of Chemical Formulae 11a to 11h:

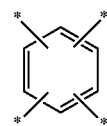

(11a)

-continued

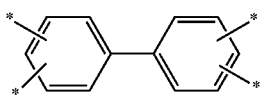
(11b)

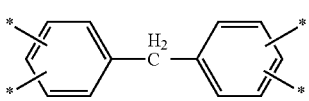
(11c)

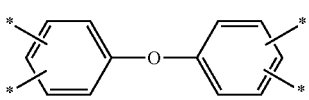
(11d)

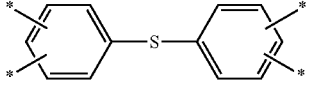
(11e)

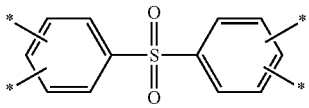
(11f)

-continued

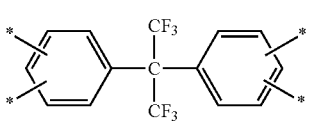
(11g)

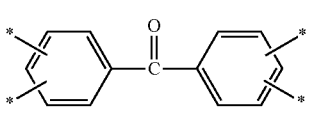
(11h)

2. The transparent film according to claim 1, wherein the transparent film has a haze value of 2 or less and a yellowness index of 20 or less.

3. The transparent film according to claim 1, wherein the transparent film has a coefficient of thermal expansion (CTE) in a range from 0 ppm/° C. to 50 ppm/° C. at a temperature ranging from 50° C. to 200° C., and has an E (%) calculated according to Formula 1 of −20≤E<0 and a K (%) calculated according to Formula 2 of 0≤K≤20 as measured 2 m+1 times (m is an integer of 1 to 3) at the temperature range from 50° C. to 200° C.:

(Minimum CTE value−Average CTE value)/Average CTE value×100=$E$  [Formula 1]

(Maximum CTE value−Average CTE value)/Average CTE value×100=$K$  [Formula 2].

4. The transparent film according to claim 1, wherein the transparent film which has a haze value of 2 or less.

5. A display device comprising the transparent film according to claim 2.

6. The transparent film according to claim 1, wherein the Q1 and Q2 are each independently selected from a C1-5 fluoroaklyl group.

7. The transparent film according to claim 1, wherein the transparent film has an absorbance in a range from 0.1 to 0.9 as measured at 308 nm and a thickness of 1 cm.

8. A transparent film for a flexible substrate of display device comprising a polymer comprising: at least one repeating unit of Chemical Formula 20:

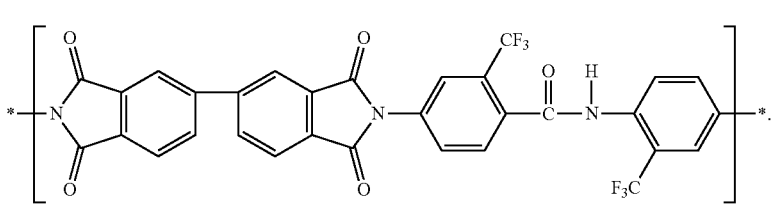
[Chemical Formula 20]

9. The transparent film according to claim 1, wherein the transparent film has a yellowness index of 20 or less.

10. The transparent film according to claim 1, wherein the transparent film has a coefficient of thermal expansion (CTE) in a range from 0 ppm/° C. to 50 ppm/° C. at a temperature ranging from 50° C. to 200° C.

11. The transparent film according to claim 1, wherein the transparent film has an E (%) calculated according to Formula 1 of −20≤E≤0 and a K (%) calculated according to Formula 2 of 0≤K≤20 as measured 2 m+1 times (m is an integer of 1 to 3) at the temperature range from 50° C. to 200° C.:

(Minimum CTE value−Average CTE value)/Average CTE value ×b 100=$E$  [Formula 1]

(Maximum CTE value−Average CTE value)/Average CTE value×100=$K$  [Formula 2]

* * * * *